(12) United States Patent
Asano et al.

(10) Patent No.: US 9,261,780 B2
(45) Date of Patent: *Feb. 16, 2016

(54) RADIATION-SENSITIVE RESIN COMPOSITION, METHOD FOR FORMING RESIST PATTERN, AND POLYMER AND COMPOUND

(75) Inventors: Yusuke Asano, Tokyo (JP); Yoshifumi Oizumi, Tokyo (JP); Akimasa Soyano, Tokyo (JP); Takeshi Ishii, Tokyo (JP)

(73) Assignee: JSR CORPORATION, Tokyo (JP)

( * ) Notice: Subject to any disclaimer, the term of this patent is extended or adjusted under 35 U.S.C. 154(b) by 132 days.

This patent is subject to a terminal disclaimer.

(21) Appl. No.: 13/699,003

(22) PCT Filed: May 19, 2011

(86) PCT No.: PCT/JP2011/061587
§ 371 (c)(1),
(2), (4) Date: Feb. 6, 2013

(87) PCT Pub. No.: WO2011/145702
PCT Pub. Date: Nov. 24, 2011

(65) Prior Publication Data
US 2013/0143160 A1 Jun. 6, 2013
US 2014/0004463 A9 Jan. 2, 2014

(30) Foreign Application Priority Data

May 20, 2010 (JP) .................. 2010-116771
Aug. 19, 2010 (JP) .................. 2010-184494

(51) Int. Cl.
| | |
|---|---|
| C08F 18/20 | (2006.01) |
| G03F 7/039 | (2006.01) |
| G03F 7/20 | (2006.01) |
| G03F 7/004 | (2006.01) |
| C08F 220/26 | (2006.01) |
| G03F 7/038 | (2006.01) |
| C07C 69/653 | (2006.01) |
| C07C 69/753 | (2006.01) |
| C07D 307/93 | (2006.01) |
| C08F 22/18 | (2006.01) |
| C08F 24/00 | (2006.01) |
| C08F 220/24 | (2006.01) |

(52) U.S. Cl.
CPC .............. *G03F 7/004* (2013.01); *C07C 69/653* (2013.01); *C07C 69/753* (2013.01); *C07D 307/93* (2013.01); *C08F 22/18* (2013.01); *C08F 24/00* (2013.01); *C08F 220/26* (2013.01); *G03F 7/0046* (2013.01); *G03F 7/0382* (2013.01); *G03F 7/0392* (2013.01); *G03F 7/2041* (2013.01); *C08F 220/24* (2013.01)

(58) Field of Classification Search
CPC ...... C08F 220/18; C08F 222/18; G03F 7/004; G03F 7/028; G03F 7/039; G03F 7/0392; G03F 7/2041

USPC ........ 526/242, 245; 430/270.1, 326, 907, 910
See application file for complete search history.

(56) References Cited

U.S. PATENT DOCUMENTS

| | | | |
|---|---|---|---|
| 4,491,628 | A | 1/1985 | Ito et al. |
| 5,360,876 | A | 11/1994 | Burgoyne et al. |
| 5,374,681 | A | 12/1994 | Kroner et al. |

(Continued)

FOREIGN PATENT DOCUMENTS

| | | |
|---|---|---|
| EP | 2479614 | 7/2012 |
| JP | 59-45439 | 3/1984 |

(Continued)

OTHER PUBLICATIONS

Office Action with Form PTO-892 Notice of References Cited issued by the U.S. Patent and Trademark Office for the U.S. Appl. No. 13/459,023, Nov. 6, 2013.
U.S. Office Action for U.S. Appl. No. 13/459,023, Apr. 17, 2013.
International Search Report for corresponding International Application No. PCT/JP2011/061587, Jun. 21, 2011.
International Search Report for corresponding International Application No. PCT/JP2011/061588, Aug. 16, 2011.
Office Action issued on Jul. 17, 2014, in U.S. Appl. No. 13/699,007, filed Jan. 30, 2013.
Office Action issued Aug. 5, 2014 in Japanese Patent Application No. 2012-515932 with English language translation.

(Continued)

*Primary Examiner* — Anca Eoff
(74) *Attorney, Agent, or Firm* — Oblon, McClelland, Maier & Neustadt, L.L.P.

(57) ABSTRACT

A radiation-sensitive resin composition that provides a resist coating film in a liquid immersion lithography process is provided, the radiation-sensitive resin composition being capable of exhibiting a great dynamic contact angle during exposure, whereby the surface of the resist coating film can exhibit a superior water draining property, and the radiation-sensitive resin composition being capable of leading to a significant decrease in the dynamic contact angle during development, whereby generation of development defects can be inhibited, and further shortening of a time period required for change in a dynamic contact angle is enabled. A radiation-sensitive resin composition including (A) a polymer having a structural unit (I) represented by the following formula (1), and (B) a radiation-sensitive acid generator.

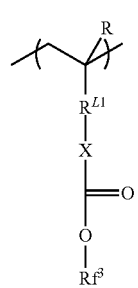

(1)

21 Claims, No Drawings

(56) References Cited

U.S. PATENT DOCUMENTS

| | | |
|---|---|---|
| 5,744,537 A | 4/1998 | Brunsvold et al. |
| 8,580,480 B2 | 11/2013 | Asano et al. |
| 2005/0277059 A1 | 12/2005 | Kanda |
| 2007/0134590 A1 | 6/2007 | Fukuhara et al. |
| 2007/0178405 A1 | 8/2007 | Kanda et al. |
| 2008/0090173 A1 | 4/2008 | Harada et al. |
| 2009/0047602 A1 | 2/2009 | Furuya et al. |
| 2009/0197204 A1 | 8/2009 | Shiono et al. |
| 2009/0202943 A1 | 8/2009 | Ohsawa et al. |
| 2009/0202945 A1 | 8/2009 | Nakagawa et al. |
| 2009/0311627 A1 | 12/2009 | Kurosawa et al. |
| 2010/0221659 A1 | 9/2010 | Ebata et al. |
| 2010/0233626 A1* | 9/2010 | Shimizu et al. ............ 430/285.1 |
| 2010/0233636 A1 | 9/2010 | Kuramoto |
| 2010/0255416 A1 | 10/2010 | Kouno et al. |
| 2010/0310985 A1* | 12/2010 | Mori et al. ................ 430/270.1 |
| 2011/0151381 A1* | 6/2011 | Hasegawa et al. ......... 430/285.1 |
| 2011/0223537 A1 | 9/2011 | Ebata et al. |
| 2012/0077126 A1* | 3/2012 | Mori et al. ................ 430/285.1 |
| 2013/0122426 A1* | 5/2013 | Osaki et al. ............... 430/285.1 |
| 2013/0143160 A1 | 6/2013 | Asano et al. |

FOREIGN PATENT DOCUMENTS

| | | |
|---|---|---|
| JP | 06-012452 B | 5/1984 |
| JP | 59-093448 | 5/1984 |
| JP | 05-188598 | 7/1993 |
| JP | 2003-183226 | 7/2003 |
| JP | 2005-352384 | 12/2005 |
| JP | 2006-276458 | 10/2006 |
| JP | 2007-279664 | 10/2007 |
| JP | 2007-304537 | 11/2007 |
| JP | 2008-088343 | 4/2008 |
| JP | 2009-134088 | 6/2009 |
| JP | 2009-139909 | 6/2009 |
| JP | 2009-217253 | 9/2009 |
| JP | 2009-271442 | 11/2009 |
| JP | 2010-020284 | 1/2010 |
| JP | 2010-032994 | 2/2010 |
| JP | 2010-066503 | 3/2010 |
| JP | 2010-204187 A | 9/2010 |
| JP | 2010-210953 | 9/2010 |
| JP | 2010-266857 A | 11/2010 |
| JP | 2010-275498 A | 12/2010 |
| JP | 2011-053360 A | 3/2011 |
| JP | 2011-132273 A | 7/2011 |
| JP | 2011-162768 A | 8/2011 |
| JP | 2011-227290 A | 11/2011 |
| JP | 2011-257613 A | 12/2011 |
| JP | 2012-001711 A | 1/2012 |
| TW | 200727080 A | 7/2007 |
| TW | 201013309 A1 | 4/2010 |
| TW | 201017333 A1 | 5/2010 |
| WO | WO 2007/116664 | 10/2007 |
| WO | WO 2009/041270 | 4/2009 |
| WO | WO 2009/051088 | 4/2009 |
| WO | WO 2010/114158 | 10/2010 |
| WO | WO 2010/114176 | 10/2010 |
| WO | WO 2010/140483 * | 12/2010 |
| WO | WO 2011/034176 | 3/2011 |
| WO | WO 2011/072307 A2 | 6/2011 |
| WO | WO 2011/072307 A3 | 6/2011 |
| WO | WO 2011/145702 | 11/2011 |
| WO | WO 2011/145703 | 11/2011 |

OTHER PUBLICATIONS

Office Action issued Aug. 5, 2014 in Japanese Patent Application No. 2012-515933 with English language translation.

Office Action issued Oct. 21, 2014, in Japanese Patent Application No. 2011-102492 filed Apr. 28, 2011 (w/ English-language Translation).

Taiwan Office Action dated Mar. 13, 2015 issued in TW100117805 (with English translation).

Combined Office Action and Search Report issued on Apr. 23, 2015 in Taiwanese Patent Application No. 100117806 (with English language translation).

* cited by examiner

RADIATION-SENSITIVE RESIN COMPOSITION, METHOD FOR FORMING RESIST PATTERN, AND POLYMER AND COMPOUND

TECHNICAL FIELD

The present invention relates to a chemically amplified resist composition. More specifically, the present invention relates to a radiation-sensitive resin composition which is suitably used as a resist composition for liquid immersion lithography, a method for forming a resist pattern using the composition, a polymer suited as a constitutive component of the composition, and a compound suited as a monomer of the polymer.

BACKGROUND ART

In the field of microfabrication typified by production of integrated circuit devices, fine resist patterns have been conventionally formed by: forming a resist coating film on a substrate with a resin composition containing a polymer having an acid-dissociable group; irradiating the resist coating film through a mask pattern with a radioactive ray having a short wavelength such as an excimer laser to permit exposure; and removing light-exposed sites with an alkaline developer. In this process, a chemically amplified resist provided by including in a resin composition a radiation-sensitive acid generating agent that generates an acid upon irradiation with the radioactive ray to improve the sensitivity by the action of the acid has been used.

With respect to such a chemically amplified resist, as a method for forming still finer resist patterns having a line width of e.g., about 45 nm, utilization of a liquid immersion lithography process has been increasing. In this method, exposure is carried out in a state in which an exposure light path space (between a lens and a resist coating film) is filled with a liquid immersion medium having a greater refractive index (n) as compared with that of the air or an inert gas such as, for example, pure water, a fluorinated inert liquid, etc. Therefore, it is advantageous in that even if a numerical aperture (NA) of a lens is increased, the focal depth is less likely to decrease, and higher resolving ability can be achieved.

Demands for a resin composition used in a liquid immersion lithography process have included: suppression of elution of the acid generating agent and the like from the formed resist coating film to the liquid immersion medium, thereby preventing deterioration of performances of the coating film and prevention of contamination of the apparatus such as a lens; and improvement of water draining property of the surface of the resist coating film to prevent leftover of watermarks, thereby enabling exposure by high speed scanning. Although Japanese Unexamined Patent Application, Publication No. 2005-352384 has proposed a technique of forming an upper layer film (protective film) on a resist coating film as a means for accomplishing such demands, a film formation step is separately required making the operation complicated. Therefore, methods for enhancing the hydrophobicity of the surface of the resist coating film have been studied, and for example, PCT International Publication No. 2007/116664 has proposed a resin composition containing a highly hydrophobic fluorine-containing polymer.

However, when the hydrophobicity of a resist coating film is enhanced, surface wettability for a developer and a rinse liquid is deteriorated; therefore, removal of development residues deposited during the development on the surface of the resist at sites unexposed with light may be insufficient, whereby development defects such as a blob may occur. For the purpose of preventing such development defects, Japanese Unexamined Patent Application, Publication No. 2010-032994 has proposed a fluorine-containing polymer that is hydrophobic during liquid immersion lithography but the hydrophobicity decreases upon development with an alkali, specifically, a fluorine-containing polymer that includes a carboxylic acid into which a fluoroalkyl group has been introduced.

In these documents, a change of hydrophobicity of the resist coating film was confirmed using a static contact angle for water as a marker. However, as a marker concerning the aforementioned water draining property which matters in practical liquid immersion lithography processes, a dynamic contact angle such as a receding contact angle rather than a static contact angle is believed to be more significant. In addition, for shortening of the time period of a development process, it is also desired to cause the change of the dynamic contact angle within a shorter period of time during a treatment with a developer. In this regard, a degree of a decrease in a dynamic contact angle after the development with an alkali of the fluorine-containing polymer, and a time period required for change in a contact angle indicated in the documents described above cannot sufficiently contribute to improvement in practical liquid immersion lithography processes.

PRIOR ART DOCUMENTS

Patent Documents

Patent Document 1: Japanese Unexamined Patent Application, Publication No. 2005-352384

Patent Document 2: PCT International Publication No. 2007/116664

Patent Document 3: Japanese Unexamined Patent Application, Publication No. 2010-032994

SUMMARY OF THE INVENTION

Problems to be Solved by the Invention

The present invention was made in view of the foregoing circumstances, and an object of the present invention is to provide a radiation-sensitive resin composition that provides a resist coating film in a liquid immersion lithography process, the radiation-sensitive resin composition being capable of exhibiting a great dynamic contact angle during exposure, whereby the surface of the resist coating film can exhibit a superior water draining property, and the radiation-sensitive resin composition being capable of leading to a significant decrease in the dynamic contact angle during development, whereby generation of development defects can be inhibited, and further shortening of a time period required for change in a dynamic contact angle is enabled.

Means for Solving the Problems

An aspect of the present invention which was made for solving the foregoing problems provides a radiation-sensitive resin composition including:

(A) a polymer having a structural unit (I) represented by the following formula (1):

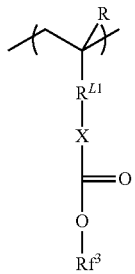
(1)

in the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a bivalent hydrocarbon group having 1 to 20 carbon atoms and having at least one fluorine atom; and (B) a radiation-sensitive acid generator.

The radiation-sensitive resin composition contains as the component (A) a polymer having the structural unit (I) represented by the above formula (1) (hereinafter, may be also referred to as "polymer (A)"), and as the component (B) a radiation-sensitive acid generator (hereinafter, may be also referred to as "acid generator (B)"). Since the polymer (A) has the aforementioned specific structural unit (I) that includes a group having a fluorine atom (hereinafter, may be also referred to as "fluorine-containing group"), the distribution thereof on the surface of the coating film is improved resulting from the extent of hydrophobicity thereof, i.e., enabling the same to be unevenly distributed on the superficial layer of the coating film. As a result, the surface of the resist coating film will have a great dynamic contact angle without need of separately forming an upper layer film provided for the purpose of shielding the resist coating film from the liquid immersion medium. Therefore, according to the radiation-sensitive resin composition, elution of the acid generating agent and the like from the coating film can be suppressed, and a superior water draining property can be imparted to the surface of the coating film. In addition, since the fluorine-containing group generates a hydrophilic group upon dissociation by hydrolysis in development with an alkali, hydrophobicity of the surface of the resist coating film decreases. As a result, wettability of the surface of the resist coating film with respect to a developer and a rinse liquid is significantly improved in a development step with an alkali; therefore, generation of development defects of a resist film that results from inferior efficiency of washing with a rinse liquid can be inhibited.

The structural unit (I) is preferably a structural unit (I-1) represented by the following formula (I-1):

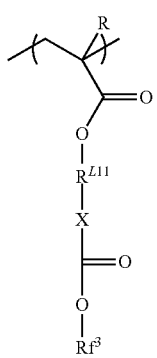
(I-1)

in the formula (I-1), $R^{L11}$ represents a single bond or a bivalent linking group; and R, $Rf^3$ and X are as defined in the above formula (1).

When the structural unit (I) has the structure specified above, polymerizability of the structural unit (I) becomes superior, thereby resulting in an increase in the content of the structural unit (I), and consequently effects of the present invention are further improved.

The structural unit (I-1) is preferably at at least one selected from the group consisting of structural units each represented by the following formulae (I-1a) to (I-1e):

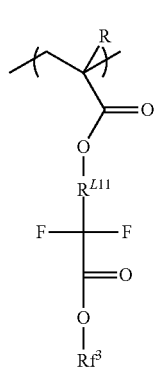
(1-1a)

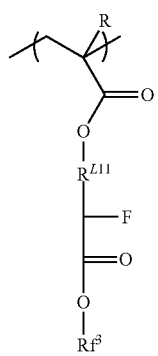
(1-1b)

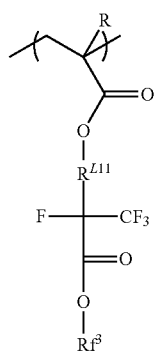
(1-1c)

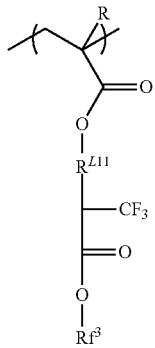

(1-1d)

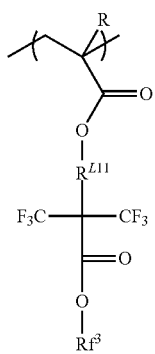

(1-1e)

in the formulae (I-1a) to (I-1e), R, $R^{L11}$ and $Rf^3$ are as defined in the above formula (I-1).

When the structural unit (I-1) has the structure described above, the reaction rate of hydrolysis in the development with an alkali is markedly improved resulting from the intensity of an electron-withdrawing property, whereby the dynamic contact angle of the surface of the coating film is further decreased.

The $Rf^3$ is preferably at least one selected from the set consisting of groups each represented by the following formulae $(Rf^3\text{-a})$ to $(Rf^3\text{-d})$:

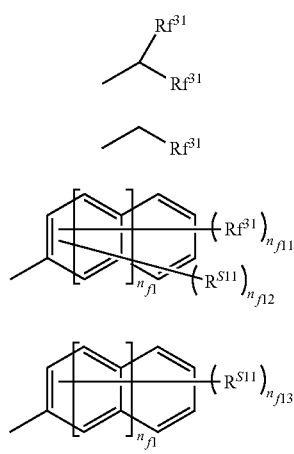

in the formulae $(Rf^3\text{-a})$ to $(Rf^3\text{-d})$, $Rf^{31}$ each independently represents a monovalent organic group having a fluorine atom; $R^{S11}$ each independently represents a substituent; $n_{f1}$ is each independently 0 or 1; $n_{f11}$ is an integer of 1 to $(5+2n_{f1})$; $n_{f12}$ is an integer of 0 to $(5+2n_{f1})$, wherein an inequality of: $(n_{f11}+n_{f12}) \le (5+2n_{f1})$ is satisfied; and $n_{f13}$ is an integer of 0 to $(5+2n_{f1})$.

When the $Rf^3$ is at least one selected from the set consisting of groups each represented by the above formulae $(Rf^3\text{-a})$ to $(Rf^3\text{-d})$, the dynamic contact angle of the surface of the coating film is further decreased.

The content of the structural unit (I) in the polymer (A) is preferably no less than 30 mol % and no greater than 100 mol %. When the content falls within this range, a satisfactory decrease in the dynamic contact angle by development can be achieved along with a great dynamic contact angle in liquid immersion lithography.

In the radiation-sensitive resin composition, it is preferred that the polymer (A) further has at least one structural unit selected from the group consisting of a structural unit (II) represented by the following formula (2) and a structural unit (III) represented by the following formula (3).

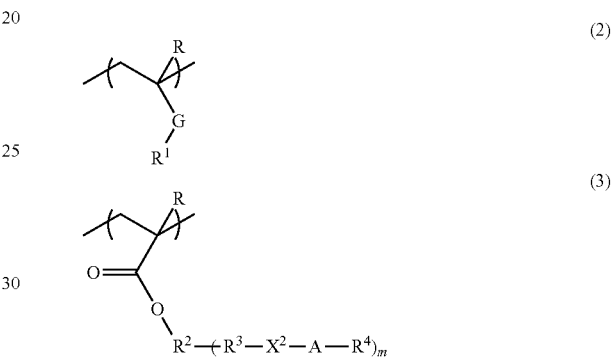

In the formulae (2) and (3), R represents a hydrogen atom, a methyl group or a trifluoromethyl group.

In the formula (2), G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom.

In the formula (3), $R^2$ represents a hydrocarbon group having a valency of (m+1) and having 1 to 20 carbon atoms, and a structure in which $R^2$ has an oxygen atom, a sulfur atom, —NR'— (wherein, R' represents a hydrogen atom or a monovalent organic group), a carbonyl group, —CO—O— or —CO—NH— which is bound to an end of $R^3$ side is acceptable; $R^3$ represents a single bond, a bivalent chain hydrocarbon group having 1 to 10 carbon atoms or a bivalent alicyclic hydrocarbon group having to 20 carbon atoms; $X^2$ represents a single bond, or a bivalent chain hydrocarbon group having 1 to 20 carbon atoms and having at least one fluorine atom; A represents an oxygen atom, —NR"— (wherein, R" represents a hydrogen atom or a monovalent organic group), —CO—O—* or —SO$_2$—O—* ("*" denotes a site bound to $R^4$); $R^4$ represents a hydrogen atom or a monovalent organic group; and m is an integer of 1 to 3, wherein in a case where m is 2 or 3, a plurality of $R^3$s, $X^2$s, As and $R^4$s are each independent.

When the polymer (A) further has at least one structural unit selected from the group consisting of the structural unit (II) and the structural unit (III), a degree of change of the dynamic contact angle in a development step of a resist coating film formed from the radiation-sensitive resin composition can be further increased.

It is preferred that the radiation-sensitive resin composition further contains (C) a polymer having a content of fluorine atoms less than that of the polymer (A) (hereinafter, may be also referred to as "polymer (C)"), and the polymer (C) has an acid-dissociable group. Due to further containing such a polymer (C), the extent of uneven distribution of the polymer (A) on the surface of the resist film increases when a resist film is formed from a composition containing the polymer (A) and the polymer (C). As a result, the aforementioned hydrophobicity and properties of the polymer (A) that result from a decrease thereof can be more efficiently exhibited.

In the radiation-sensitive resin composition, the content of the polymer (A) is preferably no less than 0.1 parts by mass and no greater than 10 parts by mass with respect to 100 parts by mass of the polymer (C). When the content of the polymer (A) falls within the above range, segregation of the polymer (A) on the surface of the resist coating film effectively occurs; therefore, elution from the resist coating film can be further inhibited, and a dynamic contact angle of the surface of the resist coating film is further increased, whereby a water draining property can be further improved.

The method for forming a resist pattern according to another aspect of the present invention includes the steps of:

(1) forming a photoresist film on a substrate using the radiation-sensitive resin composition described above;

(2) subjecting the photoresist film to liquid immersion lithography; and (3) forming a resist pattern by developing the photoresist film subjected to the liquid immersion lithography.

Since the radiation-sensitive resin composition is used in the formation method as a photoresist composition, the surface of the coating film has a superior water breaking property, and the process time can be shortened owing to high speed scanning exposure. In addition, generation of development defects can be inhibited, whereby a favorable resist pattern can be efficiently formed.

The polymer according to an aspect of the present invention has a structural unit (I) represented by the following formula (1):

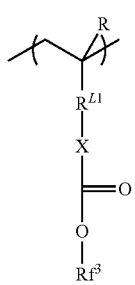

in the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a bivalent hydrocarbon group having 1 to 20 carbon atoms and having at least one fluorine atom.

In addition, it is preferred that the polymer further has at least one structural unit selected from the group consisting of a structural unit (II) represented by the following formula (2) and a structural unit (III) represented by the following formula (3).

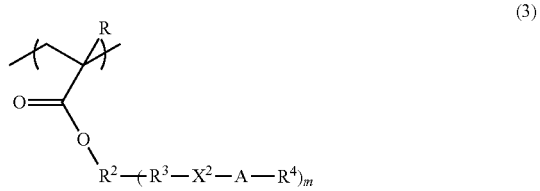

In the formulae (2) and (3), R represents a hydrogen atom, a methyl group or a trifluoromethyl group.

In the formula (2), G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom.

In the formula (3), $R^2$ represents a hydrocarbon group having a valency of (m+1) and having 1 to 20 carbon atoms, and a structure in which $R^2$ has an oxygen atom, a sulfur atom, —NR'— (wherein, R' represents a hydrogen atom or a monovalent organic group), a carbonyl group, —CO—O— or —CO—NH— which is bound to an end of $R^3$ side is acceptable; $R^3$ represents a single bond, a bivalent chain hydrocarbon group having 1 to 10 carbon atoms or a bivalent alicyclic hydrocarbon group having to 20 carbon atoms; $X^2$ represents a single bond, or a bivalent chain hydrocarbon group having 1 to 20 carbon atoms and having at least one fluorine atom; A represents an oxygen atom, —NR"— (wherein, R" represents a hydrogen atom or a monovalent organic group), —CO—O—* or —SO$_2$—O—* ("*" denotes a site bound to $R^4$); $R^4$ represents a hydrogen atom or a monovalent organic group; and m is an integer of 1 to 3, wherein in a case where m is 2 or 3, a plurality of $R^3$s, $X^2$s, As and $R^4$s are each independent.

The polymer has the aforementioned structural unit (I), and also may further have at least one structural units selected from the group consisting of the structural unit (II) and the structural unit (III). Such a polymer is characterized by having high hydrophobicity, whereas having decreased hydrophobicity due to hydrolysis; therefore, for example, the dynamic contact angle of the surface of the resist coating film can be controlled to become high during the exposure, and low after the development with an alkali. Therefore, the polymer is suitable for radiation-sensitive resin compositions and the like used in, for example, lithography techniques. The polymer has the aforementioned structural unit (I), and may further have at least one structural unit selected from the group consisting of the structural unit (II) and the structural unit (III).

The compound according to an aspect of the present invention is represented by the following formula (1):

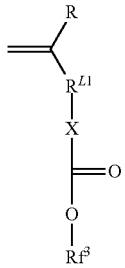

(1)

in the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a bivalent hydrocarbon group having 1 to 20 carbon atoms and having at least one fluorine atom.

Since the compound of the present invention has a structure represented by the above formula (1), it can be suitably used as a monomer for incorporating the structural unit (I) into the polymer.

Herein, a "hydrocarbon group" as merely referred to includes a chain hydrocarbon group, an alicyclic hydrocarbon group, and an aromatic hydrocarbon group. This "hydrocarbon group" may be either a saturated hydrocarbon group, or an unsaturated hydrocarbon group.

Also, the "chain hydrocarbon group" means a hydrocarbon group constituted with only a chain structure without including a ring structure in the main chain, and a linear hydrocarbon group and a branched hydrocarbon group are both included. The "alicyclic hydrocarbon group" means a hydrocarbon group that includes as a ring structure not an aromatic ring structure but only a structure of an alicyclic hydrocarbon. However, it is not necessary to be constituted with only a structure of an alicyclic hydrocarbon, and a part thereof may include a chain structure. The "aromatic hydrocarbon group" means a hydrocarbon group that includes an aromatic ring structure as a ring structure. However, it is not necessary to be constituted with only an aromatic ring structure, and a part thereof may include a chain structure or a structure of an alicyclic hydrocarbon.

Effects of the Invention

As described in the foregoing, since the radiation-sensitive resin composition of the present invention contains a polymer having a specific structural unit and a radiation-sensitive acid generator, the resist coating film formed in a liquid immersion lithography process exerts a characteristic feature of having an adequately great dynamic contact angle in exposure and a significantly decreased dynamic contact angle after the development with an alkali, and shortening of the time period required for change in a dynamic contact angle is also enabled. As a result, in addition to suppression of elution of an acid generating agent and the like from the resist coating film, due to the surface of the coating film having a superior water breaking property, high speed scanning exposure is enabled, and occurrence of development defects is inhibited since an affinity to a developer is increased in development. Accordingly, a favorable resist pattern can be formed.

DESCRIPTION OF EMBODIMENTS

Hereinafter, embodiments of the present invention will be explained in detail.

The radiation-sensitive resin composition according to an aspect of the present invention contains the polymer (A) and the acid generator (B), and preferably further contains the polymer (C). In addition, radiation-sensitive resin composition may contain an optional component as long as the effects of the present invention are not deteriorated. Hereinafter, each constitutive component will be explained in detail.

<(A) Polymer>

The polymer (A) in the embodiment of the present invention is a polymer having a structural unit (I) represented by the above formula (1). Since the polymer (A) has the structural unit (I) that includes a fluorine-containing group as specified above, the surface of the resist coating film exhibits a great dynamic contact angle resulting from high hydrophobicity of the polymer (A). Therefore, according to the radiation-sensitive resin composition, the polymer (A) is unevenly distributed on the surface of the coating film to inhibit elution of the acid generating agent and the like from the coating film, and concomitantly superior water draining property can be imparted to the surface of the coating film. In addition, since the fluorine-containing group generates a hydrophilic group upon dissociation by hydrolysis in development with an alkali, hydrophobicity of the surface of the resist coating film decreases. As a result, wettability of the surface of the coating film with respect to a developer and a rinse liquid is significantly improved in a development step with an alkali; therefore, generation of development defects of a resist film that results from inferior efficiency of washing with a rinse liquid can be inhibited.

[Structural Unit (I)]

In the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a single bond, or a bivalent chain hydrocarbon group having 1 to 20 carbon atoms and having at least one fluorine atom.

The bivalent linking group represented by $R^{L1}$ in the above formula (1) is exemplified by a bivalent chain hydrocarbon group having 1 to 30 carbon atoms, a bivalent alicyclic hydrocarbon group having 3 to 30 carbon atoms, a bivalent aromatic hydrocarbon group having 6 to 30 carbon atoms, an ether group, an ester group, a carbonyl group, an imino group, an amide group, or a bivalent group given by combination thereof. In addition, bivalent linking group may have a substituent.

Examples of the bivalent chain hydrocarbon group having 1 to 30 carbon atoms include:

alkanediyl groups such as a methanediyl group, an ethanediyl group, a propanediyl group, a butanediyl group, a pentanediyl group, a hexanediyl group, an octanediyl group, a decanediyl group, an undecanediyl group, a hexadecanediyl group and an icosanediyl group;

alkenediyl groups such as an ethenediyl group, a propenediyl group, a butenediyl group, a pentenediyl group, a hexenediyl group, an octenediyl group, a decenediyl group, an undecenediyl group, a hexadecenediyl group, and an icosenediyl group;

alkynediyl groups such as an ethynediyl group, a propynediyl group, a butynediyl group, an octynediyl group, a butadienediyl group, a hexadienediyl group and an octatrienediyl group, and the like.

Examples of the bivalent alicyclic hydrocarbon group having 3 to 30 carbon atoms include:

monocyclic saturated hydrocarbon groups such as a cyclopropanediyl group, a cyclobutanediyl group, a cyclopentanediyl group, a cyclohexanediyl group, a cycloheptanediyl group, a cyclooctanediyl group, a cyclodecanediyl group, a methylcyclohexanediyl group and an ethylcyclohexanediyl group;

monocyclic unsaturated hydrocarbon groups such as a cyclobutenediyl group, a cyclopentenediyl group, a cyclohexenediyl group, a cycloheptenediyl group, a cyclooctenediyl group, a cyclodecenediyl group, a cyclopentadienediyl group, a cyclohexadienediyl group, a cyclooctadienediyl group and a cyclodecadienediyl group;

polycyclic saturated hydrocarbon groups such as a bicyclo[2.2.1]heptanediyl group, a bicyclo[2.2.2]octanediyl group, a tricyclo[5.2.1.0$^{2,6}$]decanediyl group, a tricyclo[3.3.1.1$^{3,7}$]decanediyl group, a tetracyclo[6.2.1.1$^{3,6}$.0$^{2,7}$]dodecanediyl group and an adamantanediyl group;

polycyclic unsaturated hydrocarbon groups such as a bicyclo[2.2.1]heptenediyl group, a bicyclo[2.2.2]octenediyl group, a tricyclo[5.2.1.0$^{2,6}$]decenediyl group, a tricyclo[3.3.1.1$^{3,7}$]decenediyl group and a tetracyclo[6.2.1.1$^{3,6}$.0$^{2,7}$]dodecenediyl group, and the like.

Examples of the bivalent aromatic hydrocarbon group having 6 to 30 carbon atoms include a phenylene group, a biphenylene group, a terphenylene group, a benzylene group, a phenyleneethylene group, a phenylenecyclohexylene group and a naphthylene group, and the like.

Other bivalent linking groups are exemplified by groups represented by the following formulae (X-1) to (X-6).

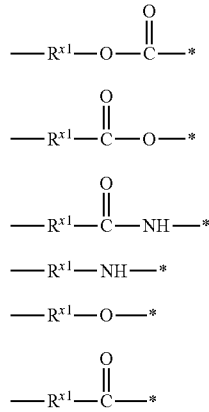

In the above formulae (X-1) to (X-6), $R^{x1}$ each independently represents a bivalent chain hydrocarbon group having 1 to 30 carbon atoms, a bivalent alicyclic hydrocarbon group having 3 to 30 carbon atoms, a bivalent aromatic hydrocarbon group having 6 to 30 carbon atoms; and "*" denotes a site bound to X in the above formula (1). The bivalent chain hydrocarbon group having 1 to 30 carbon atoms, the bivalent alicyclic hydrocarbon group having 3 to 30 carbon atoms, and the bivalent aromatic hydrocarbon group having 6 to 30 carbon atoms are exemplified by groups similar to those described above.

The bivalent hydrocarbon group having 1 to 20 carbon atoms and having at least one fluorine atom represented by X in the above formula (1) is exemplified by a bivalent chain hydrocarbon group having 1 to 20 carbon atoms, a bivalent alicyclic hydrocarbon group having 3 to 20 carbon atoms, or a bivalent aromatic hydrocarbon group having 6 to 20 carbon atoms in which a part or all hydrogen atoms thereof are substituted by a fluorine atom.

The bivalent chain hydrocarbon group having 1 to 20 carbon atoms is preferably a bivalent hydrocarbon group having 1 to 10 carbon atoms, and more preferably a bivalent hydrocarbon group having 1 to 5 carbon atoms.

The bivalent alicyclic hydrocarbon group having 3 to 20 carbon atoms is preferably a monocyclic saturated hydrocarbon group, and particularly preferably a cyclopentanediyl group, a cyclohexanediyl group, or a cyclohexylmethanediyl group.

The bivalent aromatic hydrocarbon group having 6 to 20 carbon atoms is more preferably a phenylene group, a benzylene group, and a phenethylene group. Of these, a bivalent hydrocarbon group having 1 to 5 carbon atoms is particularly preferred.

It is to be noted that X preferably has a structure in which an α-position of the carboxylate ester (i.e., a carbon atom to which COORf$^3$ bonds in the formula (1)) has a fluorine atom or a carbon atom at having a fluorine atom, and more preferably has a structure in which an α-position of the carboxylate ester has a fluorine atom or a perfluoroalkyl group. X having such a structure is preferred in light of improvement of reactivity of the polymer (A) with the developer.

X is exemplified by groups represented by the following formulae (X2-1) to (X2-6).

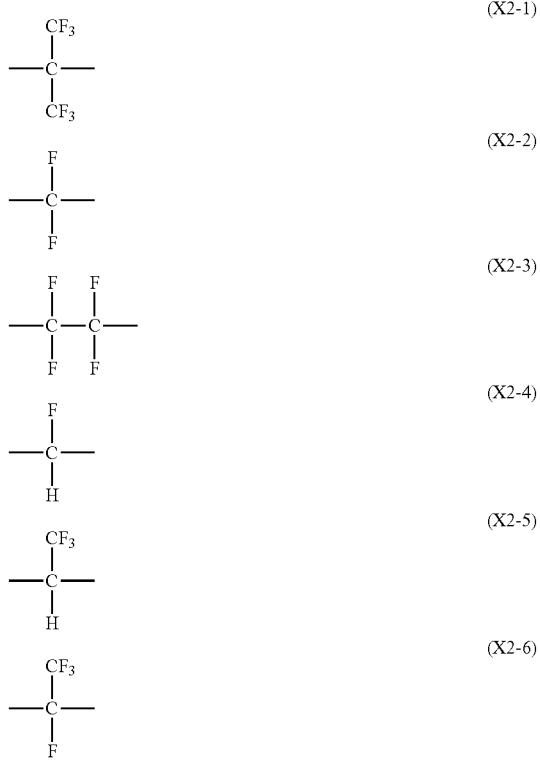

Rf$^3$ in the above formula (1) is exemplified by a monovalent aromatic hydrocarbon group which does not have or optionally has a substituent.

The monovalent aromatic hydrocarbon group is exemplified by a monovalent hydrocarbon group having benzene or naphthalene, and the like. Examples of such a hydrocarbon group include: aryl groups such as a phenyl group, a naphthyl group and a tolyl group; aralkyl groups such as a benzyl group and a phenethyl group. Examples of the substituent which may be included in the monovalent aromatic hydrocarbon group represented by $Rf^3$ include a halogen atom, —$R^{S1}$, —$R^{S2}$—O—$R^{S1}$, —$R^{S2}$—CO—$R^{S1}$, —$R^{S2}$—CO—OR, —$R^{S2}$—O—CO—R, —$R^{S2}$—CN, and the like. The $R^{S1}$ represents an alkyl group having 1 to 10 carbon atoms, a cycloalkyl group having 3 to 20 carbon atoms or an aryl group having 6 to 30 carbon atoms, and a part or all hydrogen atoms included in these groups may be substituted by a fluorine atom. The $R^{S2}$ represents a single bond, an alkanediyl group having 1 to 10 carbon atoms, a cycloalkanediyl group having 3 to 20 carbon atoms, or an arylene group having 6 to 30 carbon atoms, and a part or all hydrogen atoms included in these groups may be substituted by a fluorine atom. Among these, a halogen atom or $R^{S1}$ is preferred, and a fluorine atom, or an alkyl group having 1 to 10 carbon atoms in which a part or all hydrogen atoms may be substituted is preferred, and a fluorine atom or a trifluoromethyl group is particularly preferred. When $Rf^3$ represents a monovalent aromatic hydrocarbon group, the number of the substituent(s) included is preferably 1 to 5, more preferably 1 to 3, and particularly preferably 1 to 2.

The monovalent chain hydrocarbon group having a fluorine atom represented by $Rf^3$ in the above formula (1) is exemplified by a monovalent chain hydrocarbon group having 1 to 30 carbon atoms and having a fluorine atom.

The monovalent chain hydrocarbon group having 1 to 30 carbon atoms and having a fluorine atom is preferably a trifluoromethyl group, a 2,2,2-trifluoroethyl group, a perfluoroethyl group, a 2,2,3,3,3-pentafluoropropyl group, a 1,1,1,3,3,3-hexafluoropropyl group, perfluoro n-propyl group, a perfluoro i-propyl group, a perfluoro n-butyl group, a perfluoro i-butyl group, a perfluoro t-butyl group, a 2,2,3,3,4,4,5,5-octafluoropentyl group, a perfluorohexyl group, and the like.

The monovalent alicyclic hydrocarbon group having a fluorine atom represented by $Rf^3$ in the above formula (1) is exemplified by a monovalent alicyclic hydrocarbon group having 3 to 30 carbon atoms and having a fluorine atom.

Examples of the monovalent alicyclic hydrocarbon group having 3 to 30 carbon atoms and having a fluorine atom include monocyclic saturated hydrocarbon groups, polycyclic saturated hydrocarbon groups, polycyclic unsaturated hydrocarbon groups and the like in which at least one hydrogen atom included therein is substituted by a fluorine atom.

Among these, the group represented by $Rf^3$ is preferably at least one selected from the set consisting of groups represented by the above formulae ($Rf^3$-a) to ($Rf^3$-d), respectively, and more preferably at least one selected from the set consisting of groups represented by the above formulae ($Rf^3$-a) to ($Rf^3$-c), respectively.

In the above formulae ($Rf^3$-a) to ($Rf^3$-d), $Rf^{31}$ each independently represents a monovalent organic group having a fluorine atom; $R^{S11}$ each independently represents a substituent; $n_{f1}$ is each independently 0 or 1; $n_{f11}$ is an integer of 1 to $(5+2n_{f1})$; $n_{f12}$ is an integer of 0 to $(5+2n_{f1})$, wherein an inequality of: $(n_{f11}+n_{f12})<(5+2n_{f1})$ is satisfied; and $n_{f13}$ is an integer of 0 to $(5+2n_{f1})$.

The monovalent organic group having a fluorine atom represented by the $Rf^{31}$ is exemplified by groups similar to those described in connection with the $Rf^3$ above. Among these, a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro n-propyl group, a perfluoro i-propyl group, a perfluoro n-butyl group, a perfluoro i-butyl group, a perfluoro t-butyl group, a 2,2,3,3,4,4,5,5-octafluoropentyl group, and a perfluorohexyl group are preferred.

Examples of the monovalent organic group represented by $R^{S11}$ include —$R^{S1'}$, —$R^{S2'}$—O—$R^{S1'}$, —$R^{S2'}$—CO—$R^{S1'}$, —$R^{S2'}$—CO—OR$^{S1'}$, —$R^{S2'}$—O—CO—$R^{S1'}$, —$R^{S2'}$—CN, and the like. The $R^{S1'}$ represents an alkyl group having 1 to 10 carbon atoms, a cycloalkyl group having 3 to 20 carbon atoms or an aryl group having 6 to 30 carbon atoms. $R^{S2'}$ represents a single bond, an alkanediyl group having 1 to 10 carbon atoms, a cycloalkanediyl group having 3 to 20 carbon atoms, or an arylene group having 6 to 30 carbon atoms. Of these, —$R^{S1'}$, —$R^{S2'}$—O—$R^{S1'}$, —$R^{S2'}$—CO—$R^{S1'}$, —$R^{S2'}$—CO—OR$^{S1'}$ and —$R^{S2'}$—O—CO—$R^{S1'}$ are preferred, and —$R^{S1'}$ is more preferred.

In addition, the structural unit (I) is preferably a structural unit (I-1) represented by the above formula (1-1). When the structural unit (I) has a specified structure represented by the above formula (1-1), superior polymerizability of the structural unit (I) and a higher content of the structural unit (I) can be attained, and consequently effects of the present invention are further improved.

In the above formula (1-1), $R^{L11}$ represents a single bond or a bivalent linking group; R, $Rf^3$ and X are as defined in the above formula (1). The bivalent linking group is exemplified by groups similar to those described above.

$R^{L11}$ is preferably a single bond or a bivalent linking group exemplified in the following.

The bivalent chain hydrocarbon group having 1 to 30 carbon atoms is preferably a bivalent hydrocarbon group having 1 to 10 carbon atoms, more preferably a bivalent hydrocarbon group having 1 to 5 carbon atoms, and particularly preferably an ethanediyl group and a propanediyl group;

the bivalent alicyclic hydrocarbon group having 3 to 30 carbon atoms is preferably a monocyclic saturated hydrocarbon group, and particularly preferably a cyclopentanediyl group, a cyclohexanediyl group and a cyclohexyl methanediyl group;

the bivalent aromatic hydrocarbon group having 6 to 30 carbon atoms is more preferably a phenylene group which does not have or optionally has a fluorine atom, a benzylene group which does not have or optionally has a fluorine atom, a phenethylene group which does not have or optionally has a fluorine atom; and a bivalent group given by combining the foregoing preferred group exemplified above with an ether group, an ester group, a carbonyl group, an imino group or an amide group may be also used, and a bivalent group given by combining a bivalent hydrocarbon group having 1 to 10 carbon atoms with an ester group is more preferred.

Furthermore, the structural unit (I-1) is preferably at least one selected from the group consisting of structural units represented by the above formulae (1-1a) to (1-1e), respectively. When the structural unit (I-1) has the above-specified structure, the reaction rate of hydrolysis in the development with an alkali is markedly improved resulting from the intensity of an electron-withdrawing property, whereby the dynamic contact angle of the surface of the coating film is further decreased.

Examples of the structural units represented by the above formulae (1-1a) to (1-1e), respectively include those represented by the following formulae.

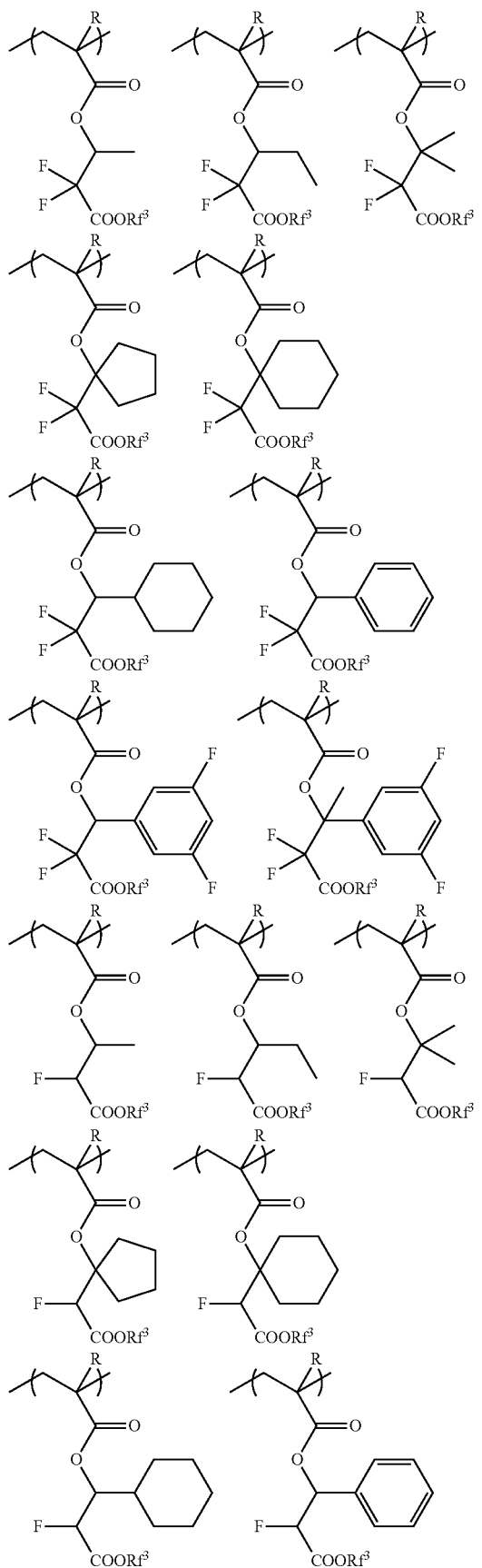

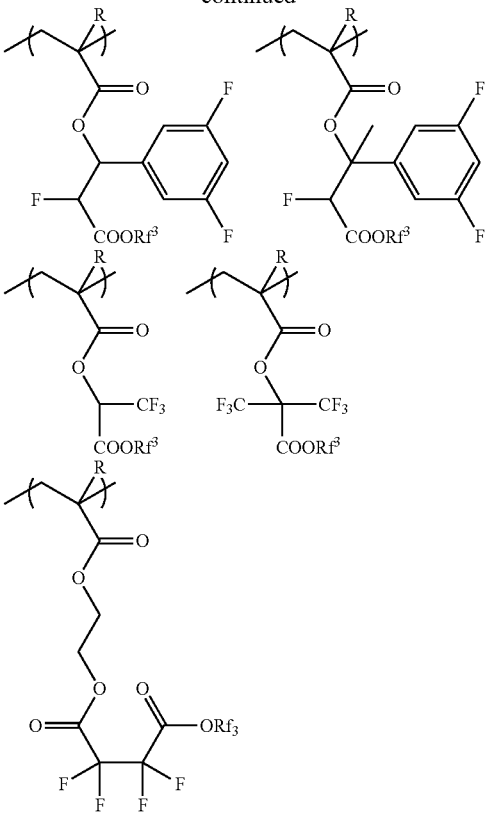

In the above formula, R and $Rf^3$ are as defined in the above formula (1).

Other specific examples of the structural unit (I) include those represented by the following formulae.

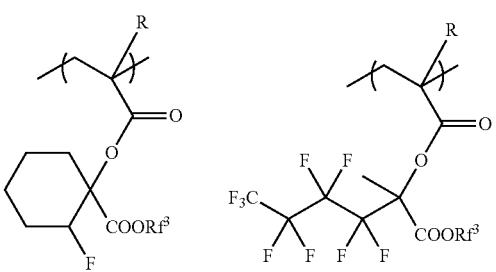

The content of the structural unit (I) with respect to the entire structural units in the polymer (A) is preferably 30 mol % to 100 mol %. When the content falls within such a range, a great dynamic contact angle in liquid immersion lithography, as well as enough decrease of the dynamic contact angle by way of the development can be achieved.

In the radiation-sensitive resin composition, it is preferred that the polymer (A) further has at least one structural unit selected from the group consisting of the structural unit (II) and the structural unit (III). When the polymer (A) further has the at least one structural unit selected from the group consisting of the structural unit (II) and the structural unit (III), a degree of change of the dynamic contact angle in a development step of the resist coating film formed from the radiation-sensitive resin composition can be further increased.

[Structural Unit (II)]

The structural unit (II) is represented by the above formula (2).

In the above formula (2), R represents a hydrogen atom, a methyl group or a trifluoromethyl group; G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom.

Examples of the chain hydrocarbon group having 1 to 6 carbon atoms and having at least one fluorine atom represented by $R^1$ include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro n-propyl group, a perfluoro i-propyl group, a perfluoro n-butyl group, a perfluoro i-butyl group, a perfluoro t-butyl group, a 2,2,3,3,4,4,5,5-octafluoropentyl group, a perfluorohexyl group, and the like.

Example of the alicyclic hydrocarbon group having 4 to 20 carbon atoms and having at least one fluorine atom represented by $R^1$ include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of the monomer that gives the structural unit (II) include trifluoromethyl(meth)acrylic acid esters, 2,2,2-trifluoroethyl(meth)acrylic acid esters, perfluoroethyl(meth)acrylic acid esters, perfluoro n-propyl(meth)acrylic acid esters, perfluoro i-propyl(meth)acrylic acid esters, perfluoro n-butyl(meth)acrylic acid esters, perfluoro i-butyl(meth)acrylic acid esters, perfluoro t-butyl(meth)acrylic acid esters, 2-(1,1,1,3,3,3-hexafluoropropyl)(meth)acrylic acid esters, 1-(2,2,3,3,4,4,5,5-octafluoropentyl)(meth)acrylic acid esters, perfluorocyclohexylmethyl(meth)acrylic acid esters, 1-(2,2,3,3,3-pentafluoropropyl)(meth)acrylic acid esters, monofluorocyclopentyl(meth)acrylic acid esters, difluorocyclopentyl(meth)acrylic acid esters, perfluorocyclopentyl (meth)acrylic acid esters, monofluorocyclohexyl(meth) acrylic acid esters, difluorocyclopentyl(meth)acrylic acid esters, perfluorocyclohexylmethyl(meth)acrylic acid esters, fluoronorbornyl(meth)acrylic acid esters, fluoroadamantyl (meth)acrylic acid esters, fluorobornyl(meth)acrylic acid esters, fluoroisobornyl(meth)acrylic acid esters, fluorotricyclodecyl(meth)acrylic acid esters, fluorotetracyclodecyl (meth)acrylic acid esters, and the like.

The content of structural unit (II) in the polymer (A) in terms of the total amount of the structural unit (II) with respect to the entire structural units constituting the polymer (A) is preferably 0 mol % to 50 mol %, more preferably 0 mol % to 30 mol %, and particularly preferably 5 mol % to 30 mol %. When the content falls within this range, a greater dynamic contact angle of the surface of the resist coating film can be provided during the liquid immersion lithography. It is to be noted that the polymer (A) may include the structural unit (II) either alone of one type, or in combination of two or more types thereof.

[Structural Unit (III)]

The structural unit (III) is represented by the above formula (3).

In the above formula (3), R represents a hydrogen atom, a methyl group or a trifluoromethyl group; $R^2$ represents a hydrocarbon group having a valency of (m+1) and having 1 to 20 carbon atoms, and a structure in which $R^2$ has an oxygen atom, a sulfur atom, —NR'— (wherein, R' represents a hydrogen atom or a monovalent organic group), a carbonyl group, —CO—O— or —CO—NH— which is bound to an end of $R^3$ side is acceptable; $R^3$ represents a single bond, a bivalent chain hydrocarbon group having 1 to 10 carbon atoms or a bivalent alicyclic hydrocarbon group having 4 to 20 carbon atoms; $X^2$ represents a single bond, or a bivalent chain hydrocarbon group having 1 to 20 carbon atoms and having at least one fluorine atom; A represents an oxygen atom, —NR"— (wherein, R" represents a hydrogen atom or a monovalent organic group), —CO—O—* or —SO$_2$—O—* ("*" denotes a site bound to $R^4$); $R^4$ represents a hydrogen atom or a monovalent organic group; and m is an integer of 1 to 3, wherein in a case where m is 2 or 3, a plurality of $R^3$s, $X^2$s, As and $R^4$s are each independent.

The $R^4$ preferably represents a hydrogen atom, since the solubility of the polymer (A) in an alkaline developer can be enhanced.

The monovalent organic group represented by the $R^4$ is exemplified by an acid-dissociable group, an alkali-dissociable group or a hydrocarbon group having 1 to 30 carbon atoms which does not have or optionally has a substituent.

The "acid-dissociable group" as referred to means a group that substitutes for a hydrogen atom in a polar functional group such as, for example, a hydroxyl group or a carboxyl group, and is dissociated in the presence of an acid. Accordingly, the structural unit (III) consequently yields a polar group by the action of an acid. Therefore, the case in which the $R^4$ is an acid-dissociable group in the above formula (3) is preferred in that the solubility of an exposed area in an alkaline developer can be increased in an exposing process in a method for forming a resist pattern described later.

The "alkali-dissociable group" as referred to means a group that substitutes for a hydrogen atom in a polar functional group such as, for example, a hydroxyl group or a carboxyl group, and is dissociated in the presence of an alkali (in, for example, 2.38% by mass aqueous solution of tetramethylammonium hydroxide at 23° C.). Accordingly, the structural unit (III) consequently yields a polar group by way of an action of an alkali. Therefore, the case in which the $R^4$ represents an alkali-dissociable group in the above formula (3) is preferred since the solubility in an alkaline developer can be improved, and the hydrophobicity of the surface of the resist coating film after the development can be further decreased.

Examples of the acid-dissociable group include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, as well as an alkoxy-substituted methyl group, an alkylsulfanyl-substituted methyl group, and the like. It is to be noted that the alkoxyl group (substituent) in the alkoxy-substituted methyl group is exemplified by an alkoxyl group having 1 to 4 carbon atoms. In addition, the alkyl group (substituent) in the alkylsulfanyl-substituted methyl group is exemplified by an alkyl group having 1 to 4 carbon atoms. In addition, the acid-dissociable group may also be group represented by a formula (Y-1) described in a paragraph of a structural unit (IV) described later. Of these, a t-butoxycarbonyl group or an alkoxy-substituted methyl group is preferred in the case in which A in the above formula (3) represents an oxygen atom or —NR"—. Alternatively, in the case in which A in the formula (3) represents —CO—O—, a group represented by a formula (Y-1) described in a paragraph of a structural unit (IV) described later is preferred.

Examples of the alkali-dissociable group include groups represented by the following formulae (W-1) to (W-4). Of these, in the case in which A in the above formula (3) represents an oxygen atom or —NR''—, a group represented by the following formula (W-1) is preferred. Alternatively, in the case in which A in the formula (3) represents —CO—O—, any one group represented by the following formulae (W-2) to (W-4) is preferred.

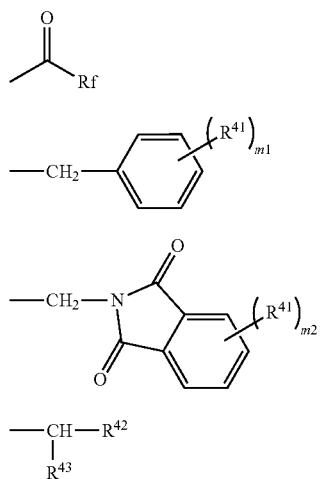

In the above formula (W-1), Rf represents a monovalent chain hydrocarbon group having 1 to 30 carbon atoms and having at least one fluorine atom, or a monovalent alicyclic hydrocarbon group having 3 to 30 carbon atoms and having at least one fluorine atom. In the formulae (W-2) and (W-3), $R^{41}$ represents a substituent, and provided that $R^{41}$ is present in a plural number, the $R^{41}$s present in plural number may be the same or different; $m_1$ is an integer of 0 to 5; and $m_2$ is an integer of 0 to 4. In the formula (W-4), $R^{42}$ and $R^{43}$ each independently represent a hydrogen atom or an alkyl group having 1 to 10 carbon atoms, and $R^{42}$ and $R^{43}$ may taken together represent an aliphatic cyclic hydrocarbon structure having 4 to 20 carbon atoms.

In the above formulae (W-2) and (W-3), the substituent represented by $R^{41}$ is exemplified by —$R^{P1}$, —$R^{P2}$—O—$R^{P1}$, —$R^{P2}$—CO—$R^{P1}$, —$R^{P2}$—O$R^{P1}$, —$R^{P2}$—O—CO—$R^{P1}$, —$R^{P2}$—OH, —$R^{P2}$—CN, —$R^{P2}$—COOH (wherein, $R^{P1}$ represents a monovalent chain saturated hydrocarbon group having 1 to 10 carbon atoms, a monovalent aliphatic cyclic saturated hydrocarbon group having 3 to 20 carbon atoms or a monovalent aromatic hydrocarbon group having to 30 carbon atoms, and a part or all hydrogen atoms included in the group may be substituted by a fluorine atom; and $R^{P2}$ represents a single bond, a bivalent chain saturated hydrocarbon group having 1 to 10 carbon atoms, a bivalent aliphatic cyclic saturated hydrocarbon group having 3 to 20 carbon atoms or a bivalent aromatic hydrocarbon group having 6 to 30 carbon atoms, or a group derived therefrom by substituting a part or all hydrogen atoms by a fluorine atom).

Also, examples of the aliphatic cyclic hydrocarbon structure represented by $R^{42}$ and $R^{43}$ taken together with the carbon atom to which $R^{42}$ and $R^{43}$ bond include a cyclopentyl group, a cyclopentylmethyl group, a 1-(1-cyclopentylethyl) group, a 1-(2-cyclopentylethyl) group, a cyclohexyl group, a cyclohexylmethyl group, a 1-(1-cyclohexylethyl) group, a 1-(2-cyclohexylethyl) group, a cycloheptyl group, a cycloheptylmethyl group, a 1-(1-cycloheptylethyl) group, a 1-(2-cycloheptylethyl) group, a 2-norbornyl group, and the like.

Preferable examples of the compound represented by the formula (W-4) include a methyl group, an ethyl group, a 1-propyl group, a 2-propyl group, a 1-butyl group, a 2-butyl group, a 1-pentyl group, a 2-pentyl group, a 3-pentyl group, a 1-(2-methylbutyl) group, a 1-(3-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(3-methylpentyl) group, a 2-(4-methylpentyl) group, a 3-(2-methylpentyl) group, and the like. Among these, a methyl group, an ethyl group, a 1-propyl group, a 2-propyl group, a 1-butyl group, and a 2-butyl group are preferred.

In the above formula (3), $X^2$ represents a bivalent chain hydrocarbon group having 1 to 20 carbon atoms and having at least one fluorine atom. Examples of $X^2$ include groups exemplified in connection with the above formulae (X2-1) to (X2-6).

When A represents an oxygen atom in the above formula (3), $X^2$ preferably represents a group represented by the above formula (X2-1). Also, when A represents —CO—O— in the above formula (3), $X^2$ preferably represents any one of groups represented by the above formulae (X2-2) to (X2-6), and more preferably represents a group represented by the above formula (X2-1).

It is to be noted that m is an integer of 1 to 3 in the above formula (3). Therefore, $R^4$ in the number of 1 to 3 is introduced into the structural unit (III). In the case where m is 2 or 3, $R^3$, $R^4$, $X^2$ and A are each independently selected. In other words, when m is 2 or 3, the $R^4$ present in a plurality of number may have the same structure or the structure different from one another. Also, when m is 2 or 3, the $R^3$ present in a plurality of number may bind to an identical carbon atom, or the distinct carbon atom of $R^2$.

The structural unit (III) is exemplified by structural units represented by the following formulae (3-1a) to (3-1c).

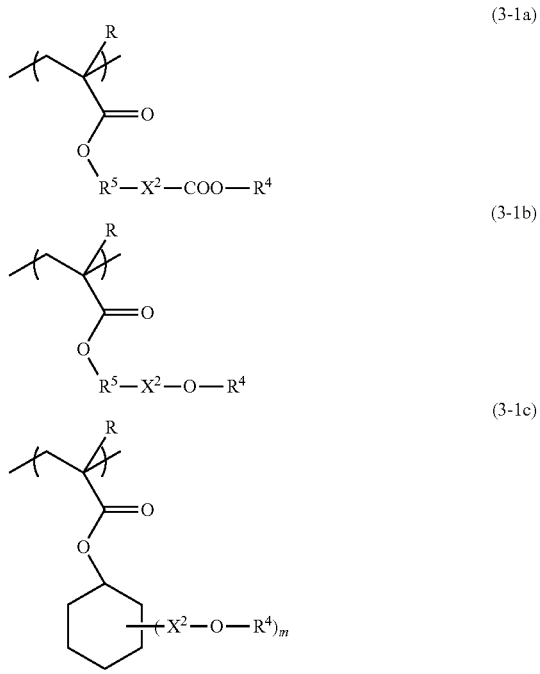

In the above formulae (3-1a) to (3-1c), $R^5$ represents a bivalent linear, branched or cyclic saturated or unsaturated hydrocarbon group having 1 to 20 carbon atoms; $X^2$, $R^4$ and m are defined in the above formula (3), and when m is 2 or 3, a plurality of $X^2$s and $R^4$s are each independent.

The monomer that gives the structural unit (III) is exemplified by compounds represented by the following formulae (3m-1) to (3m-6).

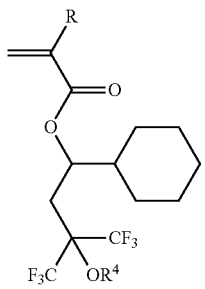

(3m-1)

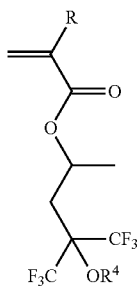

(3m-2)

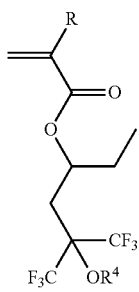

(3m-3)

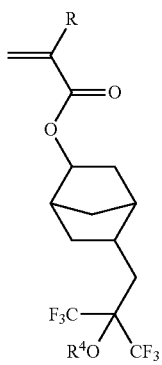

(3m-4)

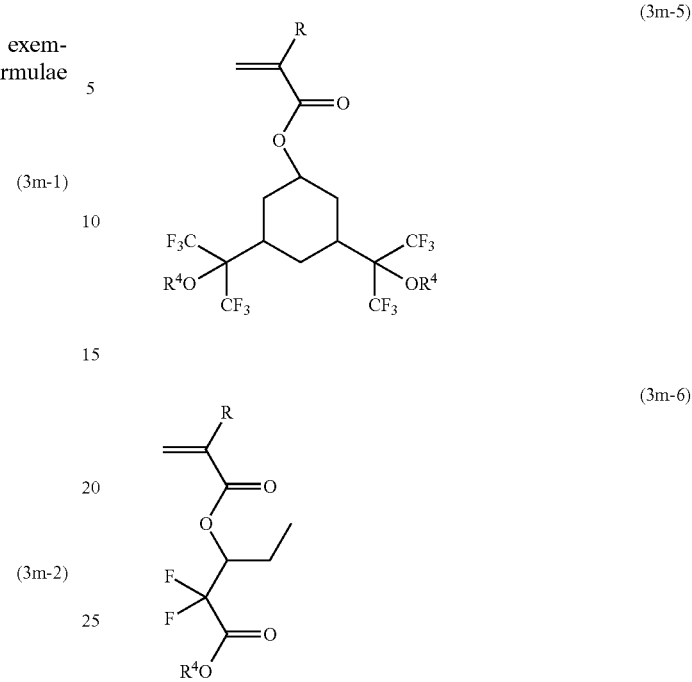

In the above formulae (3m-1) to (3m-6), R is as defined in the above formula (3); $R^4$ each independently represents a hydrogen atom or a monovalent organic group.

The content of the structural unit (III) in the polymer (A) in terms of the total amount of the structural unit (III) with respect to the entire structural units constituting the polymer (A) is preferably no greater than 50 mol %, more preferably no greater than 40 mol %, and particularly preferably no greater than 30 mol %. When the content falls within such a range, the surface of the resist coating film formed from the radiation-sensitive resin composition can attain an improved extent of decrease of the dynamic contact angle development with an alkali. It is to be noted that the polymer (A) may include the structural unit (III) either alone of one type, or in combination of two or more types thereof.

[Structural Unit (IV)]

The polymer (A) may have a structural unit (IV) represented by the following formula (4). When the polymer (A) includes the structural unit (IV), the shape of the resist pattern following the development can be further improved.

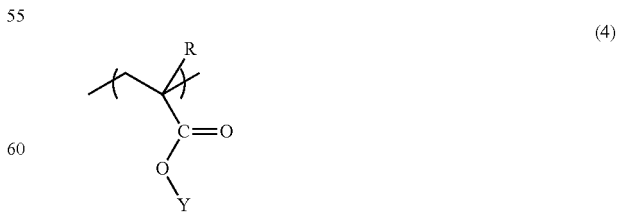

(4)

In the above formula (4), R represents a hydrogen atom, a methyl group or a trifluoromethyl group; and Y represents an acid-dissociable group.

The acid-dissociable group is preferably a group represented by the following formula (Y-1).

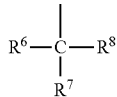
(Y-1)

In the above formula (Y-1), $R^6$ to $R^8$ each independently represent an alkyl group having 1 to 4 carbon atoms or an alicyclic hydrocarbon group having 4 to 20 carbon atoms, or $R^7$ and $R^8$ may taken together represent a bivalent alicyclic hydrocarbon group having 4 to 20 carbon atoms together with the carbon atom to which $R^7$ and $R^8$ bond.

In the above formula (Y-1), examples of the alkyl groups having 1 to 4 carbon atoms among the group represented by $R^6$ to $R^8$ include a methyl group, an ethyl group, a n-propyl group, an i-propyl group, a n-butyl group, a 2-methylpropyl group, a 1-methylpropyl group, a t-butyl group, and the like.

Examples of the monovalent alicyclic hydrocarbon group having 4 to 20 carbon atoms, or the bivalent alicyclic hydrocarbon group having 4 to 20 carbon atoms represented by $R^7$ and $R^8$ taken together with the carbon atom to which $R^7$ and $R^8$ bond include groups having a bridged skeleton such as an adamantane skeleton or a norbornane skeleton, or a cycloalkane skeleton such as cyclopentane or cyclohexane; and groups having an aliphatic cyclic hydrocarbon skeleton obtained by substituting these groups with one or more linear, branched or cyclic alkyl groups having 1 to 10 carbon atoms such as e.g., a methyl group, an ethyl group, a n-propyl group or an i-propyl group. Of these, groups having a cycloalkane skeleton are preferred in view of possibility of further improving a shape of a resist pattern after development.

The structural unit (IV) is exemplified by compounds represented by the following formulae (4-1) to (4-4).

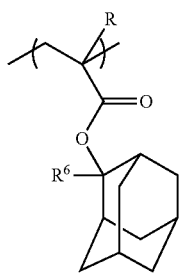
(4-1)

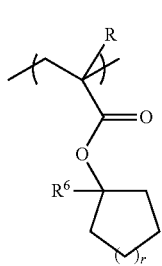
(4-2)

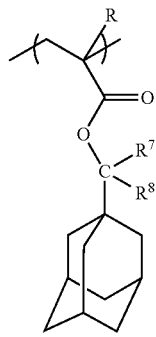
(4-3)

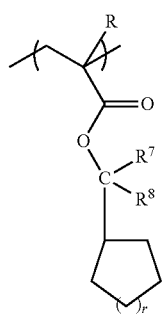
(4-4)

In the above formulae (4-1) to (4-4), R is as defined in the above formula (4); $R^6$ to $R^8$ are each independently as defined in the above formula (Y-1); $R^7$ and $R^8$ may taken together represent a bivalent alicyclic hydrocarbon group having 4 to 20 carbon atoms together with the carbon atom to which $R^7$ and $R^8$ bond; and r is an integer of 1 to 3.

The content of the structural unit (IV) in the polymer (A) in terms of the total amount of the structural unit (IV) with respect to the entire structural units constituting the polymer (A) is preferably no greater than 70 mol %, and more preferably no greater than 5 mol % to 60 mol %. When the content falls within such a range, the resist pattern configuration after development can be further improved. In addition, the polymer (A) may have the structural unit (IV) either alone, or in combination of two or more types thereof.

[Structural Unit (V)]

The polymer (A) may have a structural unit having an alkali-soluble group (hereinafter, may be also referred to as "structural unit (V)"). When the polymer (A) includes the structural unit (V), the affinity to the developer can be improved.

The alkali-soluble group in the aforementioned structural unit (V) is preferably a functional group having hydrogen atom(s) and a pKa of 4 to 11 in light of improvement of the solubility in the developer. Such a functional group is exemplified by a functional group represented by the following formulae (5s-1) and (5s-2), and the like.

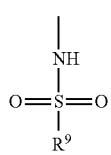
(5s-1)

(5s-2)

In the above formula (5s-1), $R^9$ represents a hydrocarbon group having 1 to 10 carbon atoms and having at least one fluorine atom.

In the above formula (5s-1), the hydrocarbon group having 1 to 10 carbon atoms and having at least one fluorine atom represented by $R^9$ is not particularly limited as long as a part or all hydrogen atoms in the hydrocarbon group having 1 to 10 carbon atoms are substituted by a fluorine atom. For example, a trifluoromethyl group or the like is preferred.

The structure for incorporating the structural unit (V) in the polymer (A) is not particularly limited, and a methacrylic acid ester, an acrylic acid ester, an α-trifluoroacrylic acid ester or the like is preferred.

The structural unit (V) is exemplified by compounds represented by the following formulae (5-1) and (5-2).

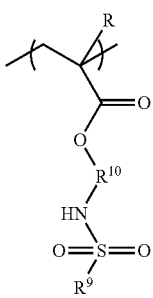
(5-1)

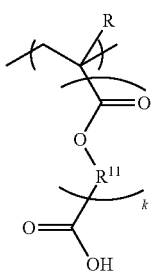
(5-2)

In the above formulae (5-1) and (5-2), R represents a hydrogen atom, a methyl group or a trifluoromethyl group; $R^9$ is as defined in the above formula (5s-1); $R^{10}$ represents a single bond, or a bivalent linear, branched or cyclic saturated or unsaturated hydrocarbon group having 1 to 20 carbon atoms. In the above formula (5-2), $R^{11}$ represents a bivalent linking group; and k is 0 or 1.

The bivalent linking group $R^{11}$ in the above formula (5-2) is exemplified by examples of the bivalent linking group in the structural unit (I), and the like.

Examples of the structural unit (V) include structural units represented by the following formulae (5-1a), (5-1b), (5-2a) to (5-2e).

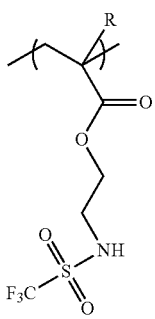
(5-1a)

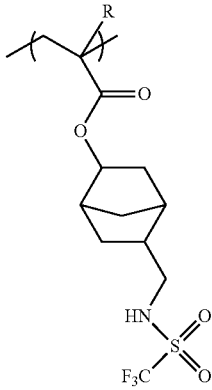
(5-1b)

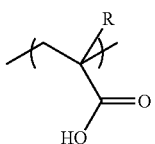
(5-2a)

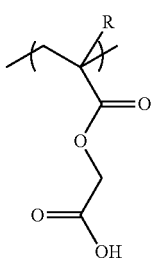
(5-2b)

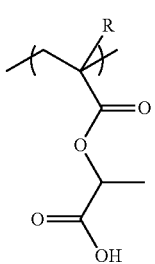
(5-2c)

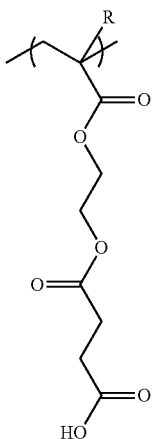

(5-2d)

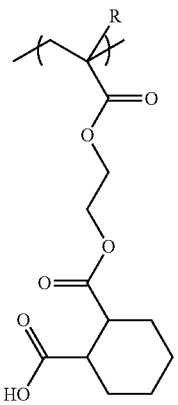

(5-2e)

In the above formulae (5-1a), (5-1b), and (5-2a) to (5-2e), R each independently represents a hydrogen atom, a methyl group or trifluoromethyl group.

The content of the structural unit (V) in the polymer (A) in terms of the total amount of the structural unit (V) with respect to the entire structural units constituting the polymer (A) is typically no greater than 50 mol %, preferably 5 mol % to 30 mol %, and more preferably 5 mol % to 20 mol %. When the content falls within such a range, securement of the water repellency during liquid immersion lithography, and the affinity to the developer during development can be achieved with a good balance.

[Structural Unit (VI)]

The aforementioned polymer (A) may have a structural unit (VI) represented by the following formula (6). When the polymer (A) includes the structural unit (VI), the affinity to the developer can be improved.

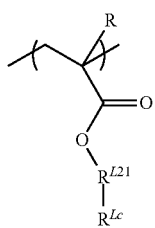

(6)

In the above formula (6), R represents a hydrogen atom, a methyl group or a trifluoromethyl group; $R^{L21}$ represents a single bond or a bivalent linking group; and $R^{Lc}$ represents a monovalent organic group having a lactone structure or a monovalent organic group having a cyclic carbonate structure.

The bivalent linking group $R^{L21}$ in the above formula (6) is exemplified by examples of the bivalent linking group in the structural unit (I).

In the above formula (6), examples of the monovalent organic group having a lactone structure represented by $R^{Lc}$ include groups represented by the following formulae (Lc-1) to (Lc-6).

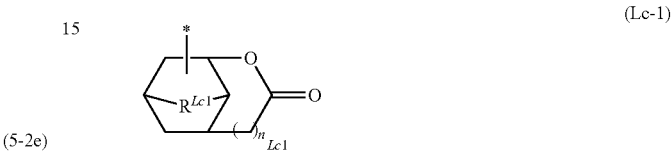

(Lc-1)

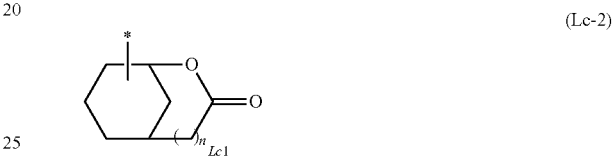

(Lc-2)

(Lc-3)

(Lc-4)

(Lc-5)

(Lc-6)

In the above formulae (Lc-1) to (Lc-6), $R^{Lc1}$ each independently represents an oxygen atom or a methylene group; $R^{Lc2}$ represents a hydrogen atom or an alkyl group having 1 to 4 carbon atoms; $n_{Lc1}$ is each independently 0 or 1; and $n_{Lc2}$ is an integer of 0 to 3; "*" denotes a site bound to $R^{L21}$ in the above formula (6); and the groups represented by the formulae (Lc-1) to (Lc-6) may have a substituent.

Specific examples of the structural unit (VI) include those disclosed in paragraphs nos. [0054] to [0057] of Japanese Unexamined Patent Application, Publication No. 2007-

304537, structural units disclosed in paragraphs nos. [0086] to [0088] of Japanese Unexamined Patent Application, Publication No. 2008-088343, and compounds represented by the following formulae (6-1a) to (6-1j).
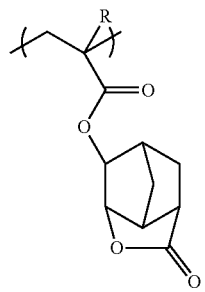
(6-1a)
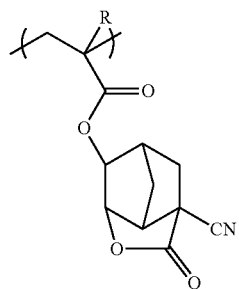
(6-1b)
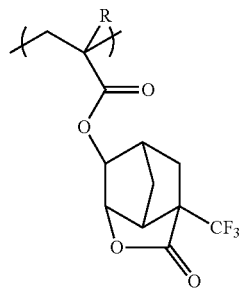
(6-1c)
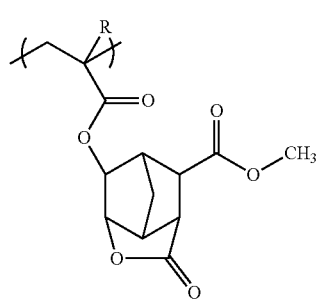
(6-1d)
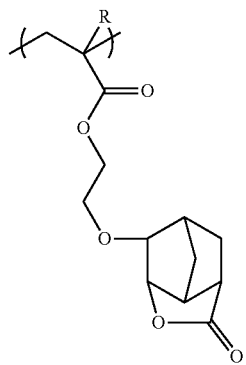
(6-1e)
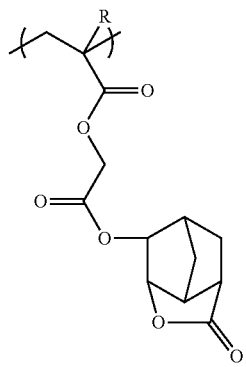
(6-1f)
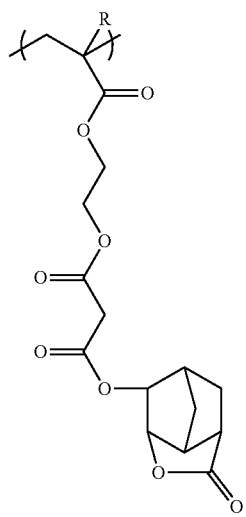
(6-1g)
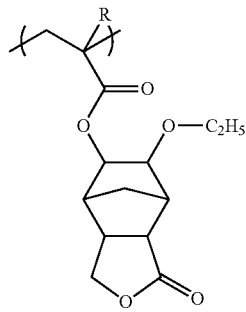
(6-1h)

-continued

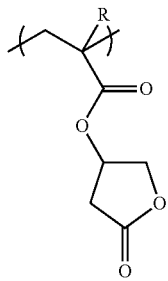
(6-1i)

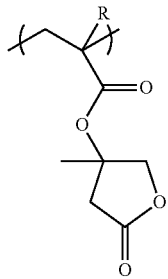
(6-1j)

In the above formulae (6-1a) to (6-1j), R represents a hydrogen atom, a methyl group or a trifluoromethyl group.

It is to be noted that the aforementioned structural unit (VI) may be included either alone or in combination of two or more types thereof. A preferable monomer that gives the structural unit (VI) is exemplified by those described in paragraph [0043] of the pamphlet of PCT International Publication No. 2007/116664.

Among the candidates of the structural unit (VI), the structural unit having a cyclic carbonate structure is exemplified by the structural unit represented by the following formula (6-2a).

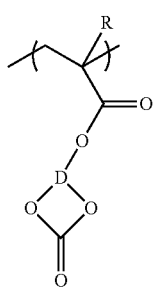
(6-2a)

In the above formula (6-2a), R is as defined in the above formula (6); D represents a trivalent chain hydrocarbon group having 1 to 30 carbon atoms, a trivalent alicyclic hydrocarbon group having 3 to 30 carbon atoms, or a trivalent aromatic hydrocarbon group having 6 to 30 carbon atoms; D may have an oxygen atom, a carbonyl group, or —NH— in its skeleton; or alternatively D may have a substituent.

The monomer that gives the structural unit represented by the above formula (6-2a) may be synthesized by conventionally well-known methods described in, for example, Tetrahedron Letters, Vol. 27, No. 32 p. 3741 (1986); and Organic Letters, Vol. 4, No. 15 p. 2561 (2002).

Preferable examples of the structural unit represented by the above formula (6-2a) include structural units represented by the above formulae (6-2a-1) to (6-2a-22).

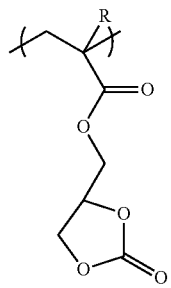
(6-2a-1)

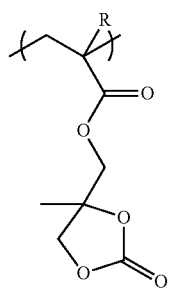
(6-2a-2)

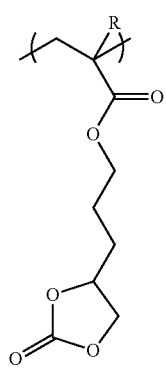
(6-2a-3)

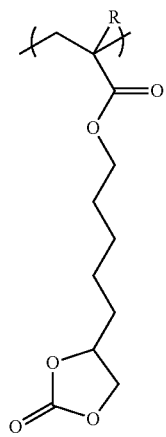
(6-2a-4)

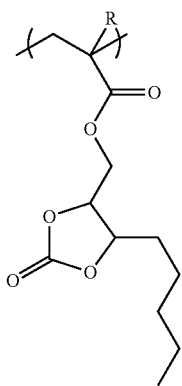 (6-2a-5)
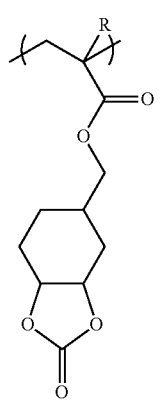 (6-2a-9)
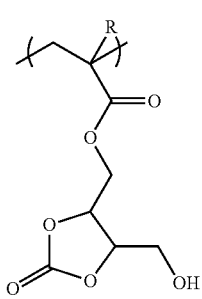 (6-2a-6)
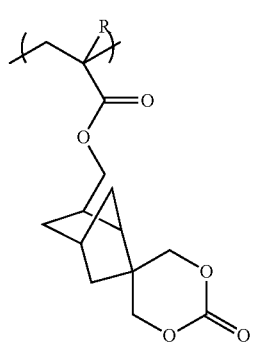 (6-2a-10)
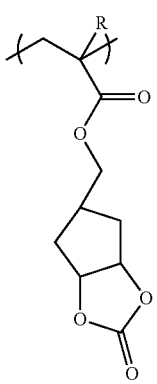 (6-2a-7)
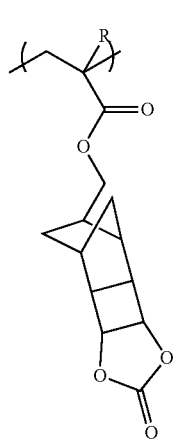 (6-2a-11)
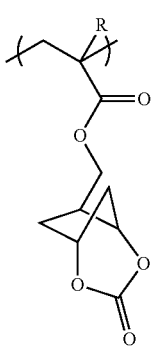 (6-2a-8)
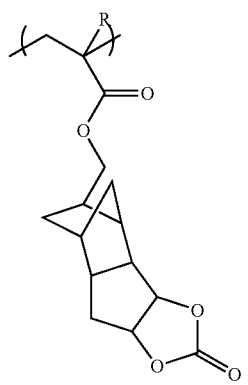 (6-2a-12)

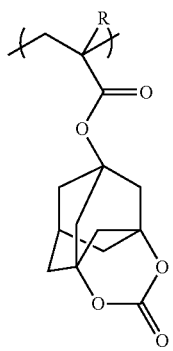 (6-2a-13)
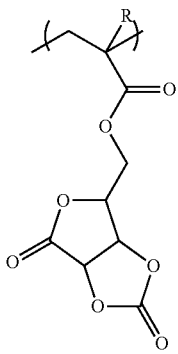 (6-2a-17)
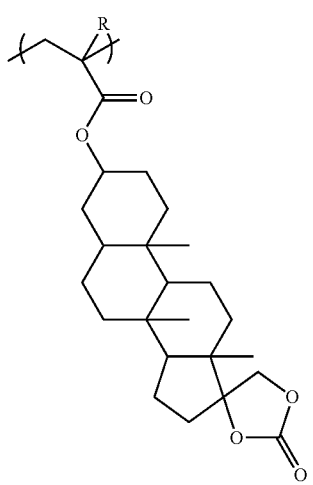 (6-2a-14)
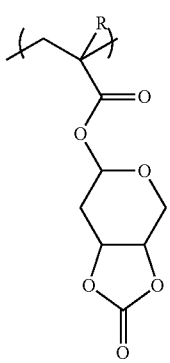 (6-2a-18)
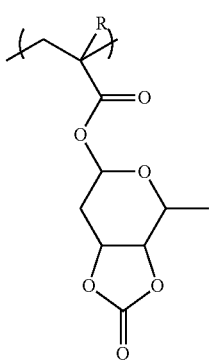 (6-2a-19)
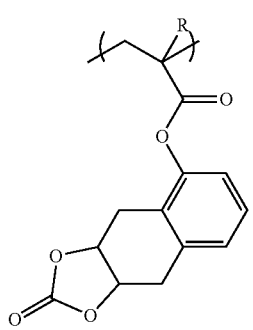 (6-2a-15)
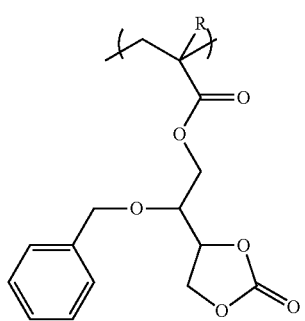 (6-2a-16)
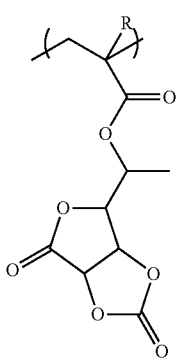 (6-2a-20)

(6-2a-21)

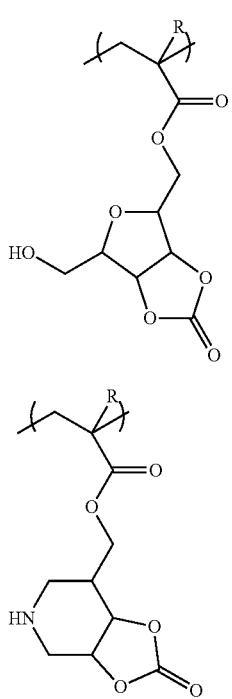

(6-2a-22)

In the above formulae (6-2a-1) to (6-2a-22), R is as defined in the above formula (6).

The content of the structural unit (VI) in the polymer (A) in terms of the total amount of the structural unit (VI) with respect to the entire structural units constituting the polymer (A) is typically no greater than 50 mol %, preferably 5 mol % to 40 mol %, and more preferably 5 mol % to 30 mol %. When the content falls within such a range, a great dynamic contact angle during the liquid immersion lithography, as well as enough decrease of the dynamic contact angle by way of the development can be achieved.

[Structural Unit (VII)]

The polymer (A) may have a structural unit (VII) represented by the following formula (7). When the polymer (A) includes the structural unit (VII), the affinity to the developer can be improved.

(7)

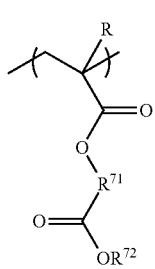

In the above formula (7), R represents a hydrogen atom, a methyl group or a trifluoromethyl group; $R^{71}$ represents a bivalent linking group not having a fluorine atom; and $R^{72}$ represents an alkali-dissociable group.

In the above formula (7), examples of the bivalent linking group not having a fluorine atom represented by $R^{71}$ include the bivalent linking groups not having a fluorine atom, in the structural unit (I).

In the above formula (7), $R^{72}$ is exemplified by groups represented by the above formulae (W-2) to (W-4).

The structural unit (VII) is exemplified by compounds represented by the following formulae (7-1) to (7-6).

(7-1)

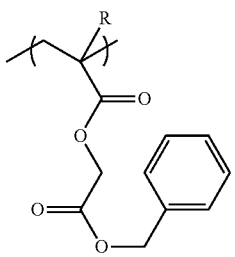

(7-2)

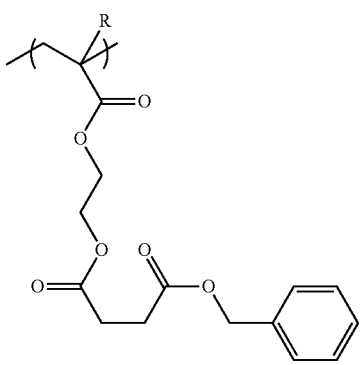

(7-3)

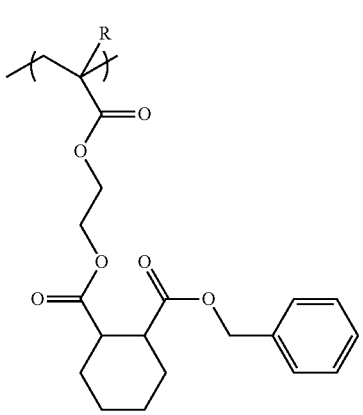

(7-4)

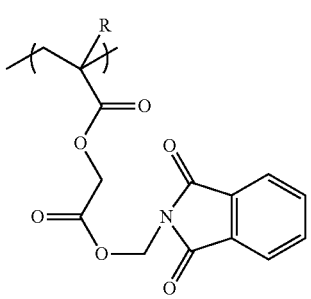

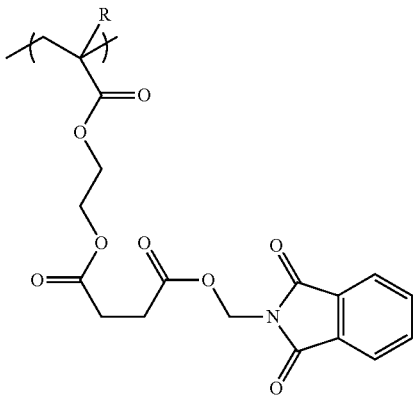

(7-5)

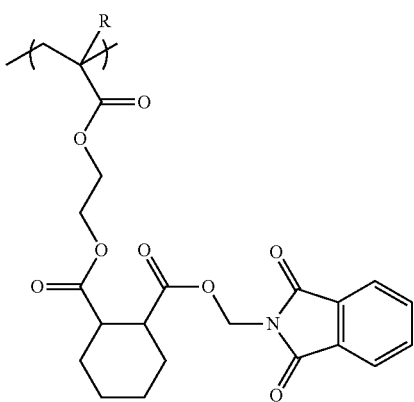

(7-6)

In the above formulae (7-1) to (7-6), R represents a hydrogen atom, a methyl group or a trifluoromethyl group.

The content of the structural unit (VII) structural unit (VI) in the polymer (A) in terms of the total amount of the structural unit (VII) with respect to the entire structural units constituting the polymer (A) is typically no greater than 50 mol %, preferably 5 mol % to 40 mol %, and more preferably 5 mol % to 20 mol %. When the content falls within such a range, a great dynamic contact angle during the liquid immersion lithography, as well as enough decrease of the dynamic contact angle by way of the development can be achieved.

The content of the polymer (A) is, with respect to the entire polymers, i.e., the total of the polymer (A) and other polymer which may be contained as needed in the radiation-sensitive resin composition, preferably 0.1% by mass to 20% by mass, more preferably 0.3% by mass to 10% by mass, and particularly preferably 0.5% by mass to 8% by mass. When the content of the polymer (A) is less than 0.1% by mass, site-dependent variation of the dynamic contact angle of the resist coating film obtained from the composition may be caused. To the contrary, when the content exceeds 20% by mass, the difference of dissolution of the resist coating film between the light-exposed site and the site unexposed with light becomes so small that the pattern configuration may be deteriorated.

[Method for Producing the Polymer (A)]

The polymer (A) may be synthesized according to a common procedure such as radical polymerization. The polymer (A) is preferably synthesized according to a method such as, e.g.:

(1) a method in which a solution containing a monomer and a radical initiator is added dropwise to a solution containing a reaction solvent or a monomer to permit a polymerization reaction; or (2) a method in which a solution containing a monomer, and a solution containing a radical initiator are each separately added dropwise to a solution containing a reaction solvent or a monomer to permit a polymerization reaction;

(3) a method in which a plurality of solutions each containing a monomer, and a solution containing a radical initiator are each separately added dropwise to a solution containing a reaction solvent or a monomer to permit a polymerization reaction.

It is to be noted that when the reaction is allowed by adding a monomer solution dropwise to a monomer solution, the amount of the monomer in the monomer solution added is preferably no less than 30 mol %, more preferably no less than 50 mol %, and particularly preferably no less than 70 mol % with respect to the total amount of the monomers used in the polymerization.

The reaction temperature in these methods may be determined ad libitum depending of the type of the initiator species. The reaction temperature is usually 30° C. to 150° C., preferably 40° C. to 150° C., and more preferably 50° C. to 140° C. The time period for the dropwise addition may vary depending on the conditions such as the reaction temperature, the type of the initiator and the monomer to be reacted, but is usually 45 min to 8 hrs, preferably 45 min to 6 hrs, and more preferably 1 hour to 5 hrs. Further, the total reaction time period including the time period for dropwise addition may also vary depending on the conditions similarly to the time period for the dropwise addition, and is typically 30 min to 12 hrs, preferably 45 min to 12 hrs, and more preferably 1 hour to 10 hrs.

The radical initiator for use in the polymerization is exemplified by azo radical initiators such as dimethyl 2,2'-azobis(2-isobutyronitrile), azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobis(2-methylpropionate); peroxide radical initiators such as benzoylperoxide, t-butylhydroperoxide and cumenehydroperoxide, and the like. Of these, dimethyl 2,2'-azobis(2-isobutyronitrile) is preferred. These may be used either alone, or in combination of two or more thereof.

As the solvent for polymerization, any solvent other than solvents that inhibit the polymerization (nitrobenzene having a polymerization inhibitory effect, mercapto compounds having a chain transfer effect, etc.), and which is capable of dissolving the monomer may be used. For example, alcohols, ethers, ketones, amides, ester-lactones, nitriles and mixed solvents thereof, and the like may be included. These solvents may be used either alone, or in combination of two or more thereof.

The polymer obtained by the polymerization reaction may be recovered preferably by a reprecipitation technique. More specifically, after the polymerization reaction is completed, the polymerization mixture is charged into a solvent for reprecipitation, whereby a target polymer is recovered in the form of powder. As the reprecipitation solvent, an alcohol, an alkane or the like may be used either alone or as a mixture of two or more thereof. Further, alternatively to the reprecipitation technique, liquid separating operation, column operation, ultrafiltration operation or the like may be employed to recover the polymer through eliminating low molecular components such as monomers and oligomers.

The polystyrene equivalent weight average molecular weight (Mw) of the polymer (A) as determined by gel permeation chromatography (GPC) is not particularly limited, and preferably 1,000 to 50,000, more preferably 1,000 to 40,000, and particularly preferably 1,000 to 30,000. The Mw of the polymer (A) being less than 1,000 may lead to failure in obtaining a resist coating film having a satisfactory dynamic contact angle. To the contrary, when the Mw of the polymer (A) exceeds 50,000, developability of the resist coating film may be inferior.

Also, the ratio (Mw/Mn) of Mw to the polystyrene equivalent number average molecular weight (hereinafter, may be also referred to as "Mn") as determined by GPC of the polymer (A) is typically 1.0 to 5.0, preferably 1.0 to 4.0, and more preferably 1.0 to 2.0.

It is to be noted that the weight average molecular weight (Mw), and the number average molecular weight (Mn) are measured by gel permeation chromatography using GPC columns manufactured by Tosoh Corporation ("G2000HXL"×2, "G3000HXL"×1 and "G4000HXL"×1), under conditions involving a flow rate of 1.0 mL/min, an elution solvent of tetrahydrofuran and a column temperature of 40° C., and with monodisperse polystyrene as a standard.

<(B) Acid Generator>

The acid generator (B) that constitutes the radiation-sensitive resin composition of the embodiment of the present invention is exemplified by onium salt compounds such as sulfonium salts and iodonium salts, organic halogen compounds, sulfone compounds such as disulfones and diazomethanesulfones, and the like. The form of the acid generator (B) contained in the radiation-sensitive resin composition may be in the form of either an acid generating agent that is a compound as described later or a form of an acid generating group incorporated as a part of the polymer (A) and/or other polymer such as the polymer (C) described later, or may be in both of these forms.

Suitable specific examples of such an acid generating agent (B) include compounds described in paragraphs nos. [0080] to [0113] of Japanese Unexamined Patent Application, Publication No. 2009-134088, and the like.

Specifically, examples of the acid generating agent (B) preferred include: diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, triphenylsulfonium trifluoromethanesulfonate, triphenylsulfonium nonafluoro-n-butanesulfonate, triphenylsulfonium perfluoro-n-octanesulfonate, cyclohexyl 2-oxocyclohexylmethylsulfonium trifluoromethanesulfonate, dicyclohexyl 2-oxocyclohexylsulfonium trifluoromethanesulfonate, 2-oxocyclohexyldimethylsulfonium trifluoromethanesulfonate, 4-hydroxy-1-naphthyldimethylsulfonium trifluoromethanesulfonate, 4-hydroxy-1-naphthyltetrahydrothiophenium trifluoromethanesulfonate, 4-hydroxy-1-naphthyltetrahydrothiophenium nonafluoro-n-butanesulfonate, 4-hydroxy-1-naphthyltetrahydrothiopheniumperfluoro-n-octanesulfonate, 1-(1-naphthylacetomethyl)tetrahydrothiophenium trifluoromethanesulfonate, 1-(1-naphthylacetomethyl)tetrahydrothiophenium nonafluoro-n-butanesulfonate, 1-(1-naphthylacetomethyl)tetrahydrothiopheniumperfluoro-n-octanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiopheniumperfluoro-n-octanesulfonate, trifluoromethanesulfonyl bicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccimidetrifluoromethanesulfonate, N-hydroxysuccimidenonafluoro-n-butanesulfonate, N-hydroxysuccimideperfluoro-n-octanesulfonate, and 1,8-naphthalenedicarboxylic acid imidetrifluoromethanesulfonate. These may be used either alone or in combination of two or more thereof.

The amount of the acid generator (B) blended with respect to 100 parts by mass of the total amount of the polymers included in the radiation-sensitive resin composition is, in light of securement of the sensitivity and developability as a resist, preferably 0.1 parts by mass to 30 parts by mass, and more preferably 0.1 parts by mass to 20 parts by mass. When the amount of the acid generating agent (B) blended is less than 0.1 parts by mass, the sensitivity and the developability tend to be inferior, whereas when the content exceeds 30 parts by mass, transparency for radioactive rays is lowered, and thus it may be difficult to obtain a rectangular resist pattern.

The radiation-sensitive resin composition preferably contains a polymer having an acid-dissociable group in addition to the polymer (A). Such a polymer having an acid-dissociable group is insoluble or hardly soluble in alkali before being subjected to an action of an acid, and becomes soluble in alkali upon dissociation of the acid-dissociable group by an action of an acid generated from the acid generator (B), etc. The phrase "insoluble or hardly soluble in alkali" as referred to for polymers means a property that in a case in which a coating film having a film thickness of 100 nm produced using only such a polymer is developed in place of the resist coating film under conditions of development with an alkali which are employed when resist patterns are formed from the resist coating film that had been formed with the radiation-sensitive resin composition, no less than 50% of the initial film thickness of the coating film remains after the development.

<(C) Polymer>

In the radiation-sensitive resin composition, it is preferred that (C) a polymer having the content of fluorine atoms lower than that of the polymer (A) is further contained, and that the polymer (C) has an acid-dissociable group. When such a polymer (C) is further contained, a degree of uneven distribution of the polymer (A) on the surface of the resist coating film is elevated when the resist coating film is formed from the composition containing the polymer (A) and the polymer (C). As a result, the hydrophobicity of the polymer (A) and characteristic features resulting from a decrease thereof can be more effectively achieved. It is to be noted that the content of fluorine atoms can be determined by $^{13}$C-NMR.

Specific structure of the polymer (C) is not particularly limited as long as it has the properties as described above, and the polymer (C) preferably has the structural unit (III) represented by the above formula (3) and the structural unit (VI) represented by the above formula (6) in regard to the polymer (A).

In the polymer (C), the content of the structural unit (III) in terms of the total amount of the structural unit (III) with respect to the entire structural units constituting the polymer (C) is preferably 0 mol % to 30 mol %, and more preferably 0 mol % to 15 mol %. When the content is greater than 30 mol %, adhesiveness to the substrate may be insufficient, whereby the pattern may be detached.

In the polymer (C), the content of the structural unit (VI) in terms of the total amount of the structural unit (VI) with respect to the entire structural units constituting the polymer (C) is preferably 5 mol % to 75 mol %, more preferably 15 mol % to 65 mol %, and particularly preferably 25 mol % to mol %. When the content is less than 5 mol %, the adhesiveness to the substrate as a resist may be insufficient, whereby the pattern may be detached. To the contrary, when the content exceeds 75 mol %, the contrast after dissolution may be impaired, whereby the pattern configuration may be deteriorated.

The polymer (C) may have other structural unit except for the structural unit (III) and the structural unit (VI) as long as it has the content of fluorine atoms described above. A polymerizable unsaturated monomer that constitutes the other structural unit is exemplified by a monomer disclosed in paragraphs nos. [0065] to [0085] of PCT International Publication No. 2007/116664A.

The other structural unit is preferably a structural unit derived from 2-hydroxyethyl(meth)acrylate, 2-hydroxypropyl(meth)acrylate, or 3-hydroxypropyl(meth)acrylate; the structural unit (V); and the like.

The Mw of the polymer (C) is typically 3,000 to 300,000, preferably 4,000 to 200,000, and more preferably 4,000 to 100,000. When the Mw is less than 3,000, the heat resistance as a resist may be deteriorated. To the contrary, when the Mw exceeds 300,000, the developability as a resist may be deteriorated.

In the radiation-sensitive resin composition, the content of the polymer (A) with respect to 100 parts by mass of the polymer (C) is preferably no less than 0.1 parts by mass and no greater than 10 parts by mass. When the content of the polymer (A) falls within the above range, segregation of the polymer (A) on the surface of the resist coating film effectively occurs; therefore, elution from the resist coating film is further suppressed, and the dynamic contact angle of the surface of the resist coating film further is further increased, whereby a water draining property can be further improved.

<Optional Components>

The optional component is exemplified by an acid diffusion controller, a solvent, an uneven distribution accelerator, a surfactant, an alicyclic compound, a sensitizing agent, a crosslinking agent, and the like. Each of these components will be described in detail below.

[Acid Diffusion Controller]

The radiation-sensitive resin composition of the embodiment of the present invention may contain an acid diffusion controller if necessary as (D) a component. The acid diffusion controller (D) is exemplified by a compound represented by the following formula (8) (hereinafter, may be also referred to as "nitrogen-containing compound (I)"), a compound having two nitrogen atoms in the same molecule (hereinafter, may be also referred to as "nitrogen-containing compound (II)"), a compound having three or more nitrogen atoms (hereinafter, may be also referred to as "nitrogen-containing compound (III)"), an amide group-containing compound, a urea compound, a nitrogen-containing heterocyclic compound, and the like. When the acid diffusion controller (D) is contained, pattern configuration and dimension fidelity as a resist can be improved. The form of the acid diffusion controller (D) contained in the radiation-sensitive resin composition may be in the form of either an acid diffusion control agent that is a compound as described later, or a form of an acid diffusion control group incorporated as a part of the polymer (A) and/or other polymer such as the polymer (C), or may be in both of these forms. The acid diffusion controller may be used either alone or in combination of two or more thereof.

In the above formula (8), $R^{12}$ to $R^{14}$ each independently represent a hydrogen atom, an optionally substituted or unsubstituted linear, branched or cyclic alkyl group, an aryl group or an aralkyl group.

Examples of the nitrogen-containing compound (I) include:

monoalkylamines such as n-hexylamine;

dialkylamines such as di-n-butylamine;

trialkylamines such as triethylamine;

aromatic amines such as aniline, and the like.

Examples of the nitrogen-containing compound (II) include ethylenediamine, N,N,N',N'-tetramethylethylenediamine, and the like.

Examples of the nitrogen-containing compound (III) include polymers such as polyethyleneimine, polyallylamine and dimethylaminoethylacrylamide, and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include pyridines such as pyridine and 2-methylpyridine, as well as pyrazine, pyrazole, and the like.

In addition, as the aforementioned nitrogen-containing organic compound, a compound having an acid-dissociable group may be also used. Examples of the nitrogen-containing organic compound having such an acid-dissociable group include N-(t-butoxycarbonyl)piperidine, N-(t-amyloxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-(t-butoxycarbonyl)-4-hydroxypiperidine, and the like.

Alternatively, as the acid diffusion controller, a compound represented by the following formula (9) may be also used.

In the above formula (9), is a cation represented by the following formula (9-1-1) or (9-1-2); $Z^-$ is $OH^-$, an anion represented by $R^{D1}$—$COO^-$, an anion represented by $R^{D1}$—$SO_3^-$, or an anion represented by $R^{D1}$—$N^-$—$SO_2$—$R^{D2}$; wherein $R^{D1}$ represents an alkyl group which is unsubstituted or optionally substituted, a monovalent alicyclic hydrocarbon group or an aryl group; $R^{D2}$ represents a monovalent alicyclic hydrocarbon group, or an alkyl group in which a part or all hydrogen atoms are substituted by a fluorine atom.

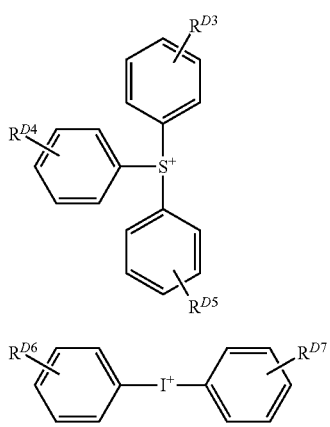

(9-1-1)

(9-1-2)

In the above formula (9-1-1), $R^{D3}$ to $R^{D5}$ each independently represent a hydrogen atom, an alkyl group, an alkoxyl group, a hydroxyl group, or a halogen atom. In the above formula (9-1-2), $R^{D6}$ and $R^{D7}$ each independently represent a hydrogen atom, an alkyl group, an alkoxyl group, a hydroxyl group, or a halogen atom.

The aforementioned compound is used as an acid diffusion controller (hereinafter, may be also referred to as "photodegradable acid diffusion controller") that loses acid diffusion controllability upon decomposition by exposure. When this compound is contained, the acid is diffused at a site exposed with light, whereas diffusion of the acid is controlled at a site unexposed with light, whereby an excellent contrast between the site exposed with light and the site unexposed with light is attained, in other words, a boundary between the light-exposed site and the site unexposed with light becomes clear. Therefore, it is particularly effective in improving the LWR (Line Width Roughness) and MEEF (Mask Error Enhancement Factor) of the radiation-sensitive resin composition of the embodiment of the present invention.

$X^+$ in the above formula (9) is a cation represented by the general formula (9-1-1) or (9-1-2) as described above. Furthermore, $R^{D3}$ to $R^{D5}$ in the above formula (9-1-1) each independently represent a hydrogen atom, an alkyl group, an alkoxyl group, a hydroxyl group or a halogen atom, and among these, a hydrogen atom, an alkyl group, an alkoxy group, and a halogen atom are preferred due to having an effect of decreasing the solubility of the compound in the developer. Moreover, $R^{D6}$ and $R^{D7}$ in the above formula (9-1-2) each independently represent a hydrogen atom, an alkyl group, an alkoxyl group, a hydroxyl group, or halogen atom, and of these, a hydrogen atom, an alkyl group, or a halogen atom is preferred.

$Z^-$ in the above formula (9) is $OH^-$, an anion represented by $R^{D1}$—$COO^-$, an anion represented by $R^{D1}$—$SO_3^-$ or an anion represented by the formula of $R^{D1}$—$N^-$—$SO_2$—$R^{D2}$, wherein, $R^{D1}$ in these formulae represents an alkyl group which is unsubstituted or optionally substituted, an alicyclic hydrocarbon group or an aryl group, and of these, an alicyclic hydrocarbon group or an aryl group is preferred due to having an effect of decreasing the solubility of the compound in the developer.

Examples of the alkyl group which is unsubstituted or optionally substituted in the above formula (9) include:

hydroxyalkyl groups having 1 to 4 carbon atoms such as a hydroxymethyl group;

alkoxyl groups having 1 to 4 carbon atoms such as a methoxy group;

a cyano group;

groups having one or more substituents such as a cyano alkyl group having 2 to 5 carbon atoms such as a cyano methyl group, and the like.

Of these, a hydroxymethyl group, a cyano group, and a cyano methyl group are preferred.

Examples of the unsubstituted or optionally substituted alicyclic hydrocarbon group in the above formula (9) include monovalent groups derived from an aliphatic cyclic hydrocarbon having e.g.: a cycloalkane skeleton such as hydroxycyclopentane, hydroxycyclohexane or cyclohexanone; a bridged aliphatic cyclic hydrocarbon skeleton such as 1,7,7-trimethyl bicyclo[2.2.1]heptan-2-one (camphor), and the like. Of these, groups derived from 1,7,7-trimethyl bicyclo [2.2.1]heptan-2-one are preferred.

Examples of the aryl group which is unsubstituted or optionally substituted in the above formula (9) include a phenyl group, a benzyl group, a phenylethyl group, a phenylpropyl group, a phenylcyclohexyl group and the like, and those obtained by substituting these compounds with a hydroxyl group, a cyano group or the like, and the like. Of these, a phenyl group, a benzyl group or a phenylcyclohexyl group is preferred.

$Z^-$ in the above formula (9) is preferably an anion represented by the following formula (9-2-1) (i.e., an anion represented by $R^{D1}$—$COO^-$, wherein $R^{D1}$ is a phenyl group), an anion represented by the following formula (9-2-2)(i.e., an anion represented by $R^{D1}$—$SO_3^-$, wherein $R^{D1}$ is a group derived from 1,7,7-trimethyl bicyclo[2.2.1]heptan-2-one) or an anion represented by the following formula (9-2-3) (i.e., an anion represented by $R^{D1}$—$N^-$—$SO_2$—$R^{D2}$, wherein $R^{D1}$ is a butyl group, and $R^{D2}$ is a trifluoromethyl group).

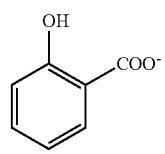

(9-2-1)

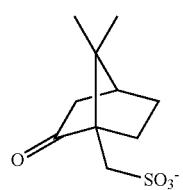

(9-2-2)

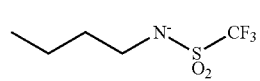

(9-2-3)

The aforementioned photodegradable acid diffusion controller is a compound represented by the general formula (9), and specifically, a sulfonium salt compound or an iodonium salt compound that meets the definition in the foregoing.

Examples of the sulfonium salt compound include triphenylsulfonium hydroxide, triphenylsulfonium salicylate, triphenylsulfonium 4-trifluoromethyl salicylate, diphenyl-4-hydroxyphenylsulfonium salicylate, triphenylsulfonium 10-camphorsulfonate, 4-t-butoxyphenyl diphenylsulfonium 10-camphorsulfonate, and the like.

Examples of the iodonium salt compound include bis(4-t-butylphenyl)iodonium hydroxide, bis(4-t-butylphenyl)iodonium salicylate, bis(4-t-butylphenyl)iodonium 4-trifluoromethyl salicylate, bis(4-t-butylphenyl)iodonium 10-camphorsulfonate, and the like.

The content of the acid diffusion controller with respect to 100 parts by mass of the total amount of the polymer included in the radiation-sensitive resin composition is preferably no greater than 10 parts by mass, and more preferably no greater than 5 parts by mass. When the acid diffusion controller is contained in an excessive amount, the resist coating film formed may have remarkably impaired sensitivity.

[Solvent]

The radiation-sensitive resin composition typically contains a solvent. The solvent is not particularly limited as long as it is a solvent that can dissolve at least the polymer (A), the acid generating agent (B), and the polymer (C) contained as desired, and the like. Examples of the solvent include linear or branched ketones;
cyclic ketones;
propylene glycol monoalkyl ether acetates;
alkyl 2-hydroxypropionates;
alkyl 3-alkoxypropionates, and the like. Among these, propylene glycol monomethyl ether acetate, and cyclohexanone are more preferred. These may be used either alone, or in combination of two or more thereof.

[Uneven Distribution Accelerator]

The uneven distribution accelerator has an effect of allowing the polymer (A) to be unevenly distributed more efficiently in the surface of the resist film. When the uneven distribution accelerator is included in the radiation-sensitive resin composition, the amount of the polymer (A) added can be reduced as compared with conventional levels. Therefore, further suppression of elution of components from a resist film into a liquid immersion liquid, and carrying out liquid immersion lithography at a high speed by high speed scanning are enabled without deteriorating fundamental characteristics as a resist such as LWR, development defects, pattern collapse resistance and the like. As a result, hydrophobicity of the surface of the resist film that inhibits defects derived from liquid immersion such as watermark defects can be enhanced. As an exemplary uneven distribution accelerator having such features, a low molecular compound having a relative permittivity of 30 or greater and no greater than 200, and a boiling point of at 1 atm (101.325 kPa) of no less than 100° C. may be used. Examples of such a compound include lactone compounds, carbonate compounds, nitrile compounds, polyhydric alcohols, and the like. These may be used either alone, or in combination of two or more thereof.

Examples of the lactone compound include γ-butyrolactone, valerolactone, mevalonic lactone, norbornanelactone, and the like.

Examples of the carbonate compound include propylene carbonate, ethylene carbonate, butylene carbonate, vinylene carbonate, and the like.

Examples of the nitrile compound include succinonitrile, and the like. Examples of the polyhydric alcohol include glycerin, and the like.

The content of the uneven distribution accelerator with respect to with respect to 100 parts by mass of the total amount of the polymer is preferably 10 parts by mass to 500 parts by mass, and more preferably 30 parts by mass to 300 parts by mass.

[Surfactant]

The surfactant is a component having actions of improving coating properties, developability, and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, as well as trade names KP341 (manufactured by Shin-Etsu Chemical Co., Ltd.), Polyflow No. 75 and Polyflow No. 95 (Kyoeisha Chemical Co., Ltd.), EFTOP EF301, EFTOP EF303 and EFTOP EF352 (Tochem Products Corporation), Megaface® F171 and Megaface® F173 (Dainippon Ink And Chemicals, Incorporated), Fluorad™ FC430 and Fluorad™ FC431 (Sumitomo 3M Limited), ASAHI GUARD AG710, Surflon S-382, Surflon SC-101, Surflon SC-102, Surflon SC-103, Surflon SC-104, Surflon SC-105 and Surflon SC-106 (Asahi Glass Co., Ltd.), and the like. These may be used either alone, or in combination of two or more thereof.

The content of the aforementioned surfactant with respect to 100 parts by mass of the total amount of the polymer included in the radiation-sensitive resin composition is typically no greater than 2 parts by mass.

[Compound Having Alicyclic Skeleton]

The alicyclic skeleton-containing compound is a component that exhibits actions of further improving the dry etching resistance, pattern configuration, adhesiveness to a substrate, and the like.

Examples of the alicyclic skeleton-containing compound include adamantane derivatives such as 1-adamantanecarboxylic acid, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[$4.4.0.1^{2,5}.1^{7,10}$]dodecane, 2-hydroxy-9-methoxycarbonyl-5-oxo-4-oxa-tricyclo[$4.2.1.0^{3,7}$]nonane, and the like. These may be used either alone, or in combination of two or more thereof.

The amount of the compound having an alicyclic skeleton blended with respect to 100 parts by mass of the total amount of the polymer included in the radiation-sensitive resin composition is typically no greater than 50 parts by mass, and preferably no greater than 30 parts by mass.

[Sensitizing Agent]

The sensitizer serves in absorbing the energy other than the energy of radioactive rays absorbed to the acid generating agent (B), and transferring the energy to the acid generator (B) in the form of, for example, electrons and/or radicals, thereby increasing the amount of acid generation, and thus has an effect of improving "apparent sensitivity" of the radiation-sensitive resin composition.

Examples of the sensitizing agent include carbazoles, acetophenones, benzophenones, naphthalenes, phenols, biacetyl, eosin, rose bengal, pyrenes, anthracenes, phenothiazines, and the like. These may be used either alone, or in combination of two or more thereof.

[Crosslinking Agent]

When the radiation-sensitive resin composition of the embodiment of the present invention is used as a negative type radiation-sensitive resin composition, a compound that enables in the presence of an acid, crosslinking of a polymer that is soluble in an alkaline developer (hereinafter, may be also referred to as "crosslinking agent") may be also blended. The crosslinking agent is exemplified by compounds having one or more types of functional groups having crosslinking reactivity with the polymer that is soluble in an alkaline developer (hereinafter, referred to as "crosslinkable functional group").

Examples of the crosslinkable functional group include glycidyl ether group, a glycidyl ester group, a glycidylamino group, a methoxymethyl group, an ethoxymethyl group, a benzyloxy methyl group, an acetoxy methyl group, a benzoyloxy methyl group, a formyl group, an acetyl group, a vinyl group, an isopropenyl group, a (dimethylamino)methyl group, a (diethylamino)methyl group, a (dimethylolamino) methyl group, a (diethylolamino)methyl group, a morpholinomethyl group, and the like.

The crosslinking agent is exemplified by those described in paragraphs nos. [0169] to [0172] of PCT International Publication No. WO2009/51088.

As the crosslinking agent, methoxymethyl group-containing compounds are preferred, and dimethoxymethylurea and tetramethoxymethylglycoluril are more preferred. These may be used either alone, or in combination of two or more thereof.

The amount of the crosslinking agent used with respect to 100 parts by mass of the polymer that is soluble in an alkaline developer is preferably 5 parts by mass to 95 parts by mass, more preferably 15 parts by mass to 85 parts by mass, and particularly preferably 20 parts by mass to 75 parts by mass. When the amount of the crosslinking agent used is less than 5 parts by mass, a decrease in the percentage of residual film, as well as meandering, swelling, etc., of the pattern are likely to occur. To the contrary, when the content exceeds 95 parts by mass, the alkali developability is likely to be decreased.

[Other Optional Component]

In addition to those described in the foregoing, a dye, a pigment, an adhesion promoter and the like may be used as the other optional component. For example, use of a dye or pigment enables a latent image at a light-exposed site to be visualized, whereby influences of halation upon exposure can be mitigated. Moreover, when an adhesion promoter is blended, the adhesiveness to a substrate can be improved. As the other additive, an alkali-soluble resin, a low molecular alkali-soluble controlling agent having an acid-dissociable protecting group, a halation inhibitor, a storage stabilizing agent, a defoaming agent, and the like may be included. These may be used either alone, or in combination of two or more thereof.

<Preparation Method of a Radiation-Sensitive Resin Composition>

The radiation-sensitive resin composition is generally prepared as a composition solution by dissolving in the solvent so as to give the total solid content of typically 1% by mass to 50% by mass, and preferably 3% by mass to 25% by mass in use, followed by filtration with a filter having a pore size of, for example, about 0.02 μm.

It is to be noted that the content of impurities such as halogen ion and metals in the radiation-sensitive resin composition is preferably as low as possible. When the content of such impurities is small, sensitivity, resolution, process stability, pattern configuration and the like of the resist coating film can be further improved. Therefore, polymers such as the polymer (A) and the polymer (C) included in the radiation-sensitive resin composition are preferably purified by, for example, washing with water, a chemical purification method such as liquid-liquid extraction, a combined method of such a chemical purification method with a physical purification such as ultrafiltration or centrifugal separation, and the like.

<Formation Method of a Photoresist Pattern>

The method for forming a resist pattern of the embodiment of the present invention includes: (1) a step of forming a photoresist film on a substrate using the radiation-sensitive resin composition (hereinafter, may be also referred to as "step (1)"), (2) a step of subjecting the photoresist film to liquid immersion lithography through a liquid for immersion lithography disposed on the photoresist film (hereinafter, may be also referred to as "step (2)"), and (3) a step of forming a resist pattern by developing the photoresist film subjected to the liquid immersion lithography (hereinafter, may be also referred to as "step (3)"). According to the formation method, since the radiation-sensitive resin composition is used as a photoresist composition, the surface of the coating film has a superior water breaking property, and the process time can be shortened owing to high speed scanning exposure. In addition, generation of development defects can be inhibited, whereby a favorable resist pattern can be efficiently formed.

In the step (1), a photoresist film is formed by coating a solution of the radiation-sensitive resin composition of the embodiment of the present invention on a substrate such as, for example, a silicon wafer, or a wafer coated with aluminum by an appropriate coating means such as means of spin coating, cast coating or roll coating. Specifically, after a solution of the radiation-sensitive resin composition is coated such that the resulting resist film has a predetermined film thickness, prebaking is carried out to allow the solvent in the coating film to be volatilized, whereby a resist film is formed.

The thickness of the resist film is preferably 10 nm to 5,000 nm, and more preferably 10 nm to 2,000 nm.

Conditions of heating in the prebaking may vary depending on the blend composition of the radiation-sensitive resin composition, and may involve preferably about 30° C. to 200° C. and more preferably 50° C. to 150° C.

In the step (2), a liquid for immersion lithography is provided on the photoresist film formed in the step (1), and a radioactive ray is irradiated through the liquid for immersion lithography to execute liquid immersion lithography of the photoresist film.

The liquid for immersion lithography is exemplified by pure water, long chain or cyclic aliphatic compounds, fluorine-based inert liquids, and the like.

The radioactive ray employed is appropriately selected from visible light rays, ultraviolet rays, far ultraviolet rays, X-rays, charged particle rays and the like in accordance with the type of the acid generator used. The radioactive ray is preferably a far ultraviolet ray typified by an ArF excimer laser (wavelength: 193 nm) or a KrF excimer laser (wavelength: 248 nm), and more preferably an ArF excimer laser (wavelength: 193 nm).

Also, conditions of the exposure such as exposure dose may be appropriately determined in accordance with the blend composition of the radiation-sensitive resin composition and the type of the additives.

In the embodiment of the present invention, a heat treatment (PEB: post exposure baking) is preferably carried out after the exposure. The PEB enables a dissociation reaction of the acid-dissociable group in the resin components to smoothly proceed. Conditions of heating of the PEB may be appropriately adjusted depending on the blend composition of the radiation-sensitive resin composition, and involve usually 30° C. to 200° C., and preferably 50° C. to 170° C.

In the embodiment of the present invention, in order to maximize the potential capability of the radiation-sensitive resin composition, an organic or inorganic antireflection film may be also formed on the substrate employed, as disclosed in, for example, Japanese Examined Patent, Publication No. H6-12452 (Japanese Unexamined Patent Application, Publication No. S59-93448), and the like. Moreover, in order to prevent influences of basic impurities etc., included in the environment atmosphere, a protective film may be also provided on the photoresist film, as disclosed in, for example, Japanese Unexamined Patent Application, Publication No.

H5-188598, and the like. Furthermore, in order to prevent effluence of the acid generator etc., from the photoresist film during the liquid immersion lithography, a protective film for liquid immersion may be provided on the photoresist film, as disclosed in, for example, Japanese Unexamined Patent Application, Publication No. 2005-352384, and the like. It is to be noted that these techniques may be used in combination.

In the method for forming a resist pattern by the liquid immersion lithography, the resist pattern can be formed with only the photoresist film obtained using the radiation-sensitive resin composition of the embodiment of the present invention, without providing the protective film (upper layer film) described above on the photoresist film. If a resist pattern is formed with the photoresist film that is free from the upper layer film, a step of forming a protective film (upper layer film) can be omitted, thereby capable of leading to expectation for improvement of throughput.

In the step (3), a predetermined resist pattern is formed by subjecting the exposed resist film to development.

Examples of preferable developer solution used in the development process include aqueous alkali solutions prepared by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene or 1,5-diazabicyclo-[4.3.0]-5-nonene.

The concentration of the alkaline aqueous solution is preferably no greater than 10% by mass. In the case in which the concentration of the alkaline aqueous solution is greater than 10% by mass, sites unexposed with light may be also dissolved in the developing solution.

An organic solvent may be also added to the developing solution consisting of the aforementioned alkaline aqueous solution. Examples of the organic solvent include ketones such as acetone, methyl ethyl ketone, methyl-1-butyl ketone, cyclopentanone, cyclohexanone, 3-methyl cyclopentanone and 2,6-dimethyl cyclohexanone;

alcohols such as methyl alcohol, ethyl alcohol, n-propyl alcohol, i-propyl alcohol, n-butyl alcohol, t-butyl alcohol, cyclopentanol, cyclohexanol, 1,4-hexanediol and 1,4-hexanedimethylol;

ethers such as tetrahydrofuran and dioxane; esters such as ethyl acetate, n-butyl acetate and i-amyl acetate; aromatic hydrocarbons such as toluene and xylene, phenol, acetonyl acetone, dimethylformamide, and the like.

These may be used either alone, or in combination of two or more thereof.

The amount of the organic solvent used is preferably no greater than 100 parts by volume with respect to 100 parts by volume of the alkaline aqueous solution. In the case in which the amount of the organic solvent used is greater than 100 parts by volume, developability is lowered, and thus undeveloped portion at the site exposed with light may increase. Moreover, to the developing solution consisting of the alkaline aqueous solution may be added an appropriate amount of a surfactant and the like. It is to be noted that the development with a developing solution consisting of the alkaline aqueous solution is, in general, followed by washing with water and drying.

<Polymer>

The polymer of the embodiment of the present invention has the structural unit (I) represented by the following formula (1).

In the above formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a single bond, or a bivalent chain hydrocarbon group having 1 to 20 carbon atoms and having at least one fluorine atom;

Moreover, it is preferred that the polymer further has at least one structural unit selected from the group consisting of the structural unit (II) represented by the above formula (2) and the structural unit (III) represented by the above formula (3).

In the above formulae (2) and (3), R represents a hydrogen atom, a methyl group or a trifluoromethyl group. In the above formula (2), G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom. In the above formula (3), $R^2$ represents a hydrocarbon group having a valency of (m+1) and having 1 to 20 carbon atoms, and a structure in which $R^2$ has an oxygen atom, a sulfur atom, —NR'— (wherein, R' represents a hydrogen atom or a monovalent organic group), a carbonyl group, —CO—O— or —CO—NH— which is bound to an end of $R^3$ side is acceptable; $R^3$ represents a single bond, a bivalent chain hydrocarbon group having 1 to 10 carbon atoms or a bivalent alicyclic hydrocarbon group having 4 to 20 carbon atoms; $X^2$ represents a single bond, or a bivalent chain hydrocarbon group having 1 to 20 carbon atoms and having at least one fluorine atom; A represents an oxygen atom, —NR"— (wherein, R" represents a hydrogen atom or a monovalent organic group), —CO—O—* or —SO$_2$—O—* ("*" denotes a site bound to $R^4$); $R^4$ represents a hydrogen atom or a monovalent organic group; and m is an integer of 1 to 3, wherein in a case where m is 2 or 3, a plurality of $R^a$s, $X^2$s, As and $R^4$s are each independent The polymer has the aforementioned structural unit (I), and also may further have at least one structural units selected from the group consisting of the structural unit (II) and the structural unit (III). Such a polymer is characterized by having high hydrophobicity, whereas having decreased hydrophobicity upon hydrolysis; therefore, for example, the dynamic contact angle of the surface of the resist coating film can be controlled to become high during the exposure, and low after the development with an alkali. Therefore, the polymer is suitable for radiation-sensitive resin compositions and the like used in, for example, lithography techniques.

The compound of the embodiment of the present invention is represented by the above formula (1).

In the above formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a single bond, or a bivalent chain hydrocarbon group having 1 to 20 carbon atoms and having at least one fluorine atom.

<Compound>

Since the compound of the embodiment of the present invention has the structure represented by the above formula (i), it can be suitably used as a monomer for incorporating the structural unit (I) into the polymer.

Detailed description of the polymer and the compound of the embodiment of the present invention is omitted here since both are described in detail in the description of the polymer (A) included in the radiation-sensitive resin composition.

The compound represented by the above formula (i) can be synthesized according to, for example, the following scheme.

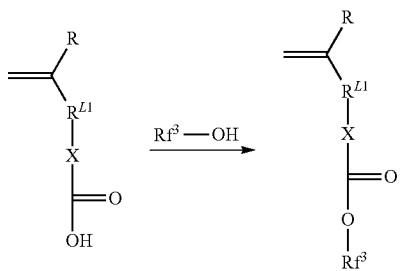

In the above formula, R, Rf³, R^{L1}, and X are as defined in the above formula (i).

The compound represented by the above formula (i) is obtained by stirring a mixture of an alcohol having a fluorine atom, and a fluorine-containing carboxylic acid in a solvent such as dichloromethane. After completing the reaction, the mixture is neutralized by adding hydrochloric acid, etc., and subjected to an appropriate treatment such as washing by liquid separation, or distillation or recrystallization, thereby enabling isolation of the compound.

EXAMPLES

Hereinafter, the present invention will be explained in detail by way of Examples, but the present invention is not to be construed as being limited to the Examples. Note that a ¹H-NMR analysis of the compound, and a ¹³C-NMR analysis for determination of the content of fluorine atoms of the polymer were carried out using a nuclear magnetic resonance apparatus (JEOL, Ltd. "JNM-ECX400").

Synthesis of Compound (i)

Example 1

Synthesis of 2,4-difluorophenyl-2,2-difluoro-3-(methacryloyloxy)pentanoate (M-1)

After a reaction vessel which had been sufficiently dried inside by vacuum heating was replaced with dry nitrogen, 100 mL of a solution of 22.22 g (0.1 mol) of 2,2-difluoro-3-(methacryloyloxy)pentanoic acid in dichloromethane was added into the reaction vessel, and the mixture was cooled to an ice temperature. Thereto was added 100 ml of a solution of 22.70 g (0.11 mol) of dicyclohexylcarbodiimide in dichloromethane over 10 min, and 0.61 g (5 mmol) of N,N-dimethyl-4-aminopyridine (DMAP) and 13.66 g (0.105 mol) of 2,4-difluorophenol were further added. Thereafter, the temperature of the reaction vessel was elevated to the room temperature, followed by stirring the mixture for 2 hrs, and 300 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off by an evaporator, followed by purification by column chromatography to give 21.73 g of 2,4-difluorophenyl-2,2-difluoro-3-(methacryloyloxy)pentanoate (M-1) (yield: 65%).

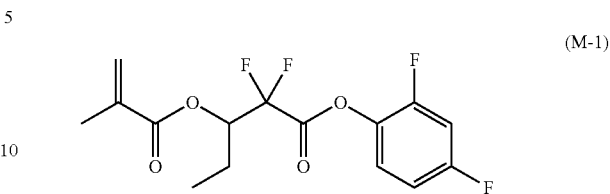

¹H-NMR (CDCl₃) δ: 1.18 (t, 3H; CH₃), 1.75-1.85 (m, 2H; CH₂—CH₃), 1.91 (s, 3H; CH₃), 5.45-5.65 (m, 1H; CH—CF₂), 5.67 (s, 1H; C═CH₂), 6.14 (s, 1H; C═CH₂), 6.80-7.00 (m, 3H; C₆H₃F₂)

Example 2

Synthesis of 3-(trifluoromethyl)phenyl-2,2-difluoro-3-(methacryloyloxy)pentanoate (M-2)

After a reaction vessel which had been sufficiently dried inside by vacuum heating was replaced with dry nitrogen, 100 mL of a solution of 22.22 g (0.1 mol) of 2,2-difluoro-3-(methacryloyloxy)pentanoic acid in dichloromethane was added into the reaction vessel, and the mixture was cooled to an ice temperature. Thereto was added 100 mL of a solution of 22.70 g (0.11 mol) of dicyclohexylcarbodiimide (DCC) in dichloromethane over 10 min, and 0.61 g (5 mmol) of DMAP and 17.02 g (0.105 mol) of 3-(trifluoromethyl)phenol were further added. Thereafter, the temperature of the reaction vessel was elevated to the room temperature, followed by stirring the mixture for 2 hrs, and 300 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off by an evaporator, followed by purification by column chromatography to give 22.71 g of 3-(trifluoromethyl)phenyl-2,2-difluoro-3-(methacryloyloxy)pentanoate (M-2) (yield: 62%).

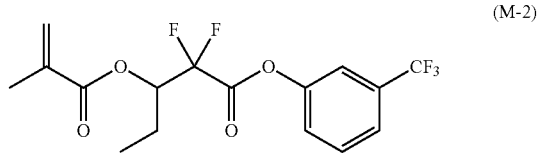 [SMILES: C=C(C)C(=O)OC(CC)C(F)(F)C(=O)Oc1cccc(C(F)(F)F)c1]

¹H-NMR (CDCl₃) δ: 1.05 (t, 3H; CH₃), 1.85-2.05 (m, 5H; CH₃, CH₂—CH₃), 5.45-5.55 (m, 1H; CH—CF₂), 5.68 (s, 1H; C═CH₂), 6.20 (s, 1H; C═CH₂), 7.30-7.70 (m, 4H; C₆H₄CF₃)

Example 3

Synthesis of 3-(trifluoromethyl)phenyl-2-fluoro-3-(methacryloyloxy)pentanoate (M-3)

After a 500 mL reaction vessel which had been sufficiently dried inside by vacuum heating was replaced with dry nitrogen, and placed in an ice bath, 24.2 g (370 mmol/1.5 equivalent) of activated metal zinc and 300 mL of THF (dehydrated) were added into the reaction vessel. Thereto was added a bromofluoroethyl acetate/THF solution (46.91 g (253.6 mmol/1.0 equivalent) of bromofluoroethyl acetate and 80 mL of THF (dehydrated)) dropwise over 5 min. After the dropwise addition, the temperature of the mixture was elevated to the room temperature, followed by stirring for 20 min. Thereto was added a propionealdehyde/THF solution (17.76 g (305.8 mmol/1.2 equivalent) of propionealdehyde and 80 mL of THF (dehydrated)), and the mixture was stirred for 60 min at a room temperature. Thereafter, water and diisopropyl ether were added thereto, and two-layer separation was carried out. The organic layer thus obtained was washed with diluted hydrochloric acid and water, and the moisture was eliminated using magnesium sulfate, followed by filtration. Then diisopropyl ether was distilled off to give 35.4 g (yield: 85%) of ethyl 2-fluoro-3-hydroxy-pentanoate represented by the following formula.

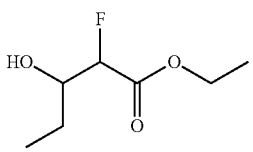

$^1$H-NMR (CDCl$_3$) δ: 1.02 (t, 3H; CH$_3$), 1.32 (t, 3H; CH$_3$), 1.52 (m, 2H), 2.45 (br, 1H; OH), 3.75 (m, 1H; CH—OH), 4.21 (q, 2H; CH$_2$—O), 4.90 (dd, 1H; CH—F)

Under a nitrogen atmosphere, 50 mL of dehydrated THF, 4.63 g (45.8 mmol) of triethylamine and 466 mg (3.82 mmol) of dimethylaminopyridine were added to 6.27 g (38.2 mmol) of the ethyl 2-fluoro-3-hydroxypentanoate at a room temperature. Thereafter, 4.39 g (42.0 mmol) of methacrylic acid chloride was added dropwise over 10 min, and then the mixture was stirred for 2 hrs. After disappearance of the raw material was confirmed by thin layer chromatography (TLC), an aqueous sodium bicarbonate solution was added to stop the reaction. Thereafter, ethyl acetate was added to the reaction liquid and extraction was carried out three times. The organic layer thus obtained was washed with water and saturated brine each once, and dried by adding anhydrous sodium sulfate. Thereafter, the product obtained by distilling off the solvent under a reduced pressure was purified by column chromatography to give 6.38 g (yield: 60%) of ethyl 2-fluoro-3-(methacryloyloxy)pentanoate represented by the following formula.

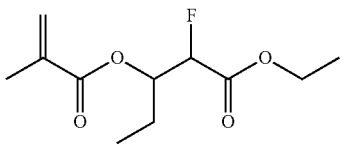 [SMILES: C=C(C)C(=O)OC(CC)C(F)C(=O)OCC]

$^1$H-NMR (CDCl$_3$) δ: 0.90 (t, 3H; CH$_3$), 1.29 (t, 3H; CH$_3$), 1.80 (m, 2H), 1.93 (s, CH$_3$), 4.27 (m, 2H; CH$_2$—O), 4.81 (m, 1H; CH—O), 4.91 (dd, 1H; CH—F), 5.62 (s, 1H; C=CH$_2$), 6.14 (s, 1H; C=CH$_2$)

Under a nitrogen atmosphere, 5.81 g (25 mmol) of the ethyl 2-fluoro-3-(methacryloyloxy)pentanoate, and 250 mL of THF were cooled in a 1 L reaction vessel on an ice bath to an ice temperature, and thereto was added 250 g of a 2.38 weight % aqueous tetramethylammoniumhydroxide solution. The temperature of the mixture was elevated to the room temperature, followed by stirring the mixture at a room temperature for 5 hrs. After disappearance of the raw material was confirmed by thin layer chromatography, the solvent of the reaction liquid was distilled off under a reduced pressure. Water was added to the reaction mixture thus obtained, and the mixture was extracted three times with ethyl acetate. The organic layer was washed with water twice, and the solvent was distilled off under a reduced pressure to obtain 4.59 g of 2-fluoro-3-(methacryloyloxy)pentanoic acid represented by the following formula (yield: 90%).

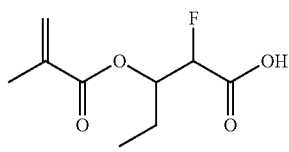

$^1$H-NMR (CDCl$_3$) δ: 0.97 (t, 3H; CH$_3$), 1.85 (m, 2H; CH$_2$), 1.93 (s, 3H; CH$_3$), 4.80 (m, 1H; CH—O), 4.85 (dd, 1H; CH—F), 5.60 (s, 1H; C=CH$_2$), 6.10 (s, 1H; C=CH$_2$), 9.65 (br, 1H; COOH)

After a reaction vessel which had been sufficiently dried inside by vacuum heating was replaced with dry nitrogen, a solution of 4.08 g of 2-fluoro-3-(methacryloyloxy)pentanoic acid (0.02 mol) in 20 mL of dichloromethane was added into the reaction vessel, and the mixture was cooled to an ice temperature. Thereto was added 20 mL of a solution of 4.54 g (0.022 mol) of DCC in dichloromethane over 10 min, and 0.12 g (1 mmol) of DMAP and 3.40 g (0.21 mol) of 3-(trifluoromethyl)phenol were further added. Thereafter, the temperature of the reaction vessel was elevated to the room temperature, followed by stirring the mixture for 2 hrs, and 100 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off by an evaporator, followed by purification by column chromatography to give 4.55 g (yield: 62%) of intended 3-(trifluoromethyl)phenyl-2-fluoro-3-(methacryloyloxy)pentanoate (M-3).

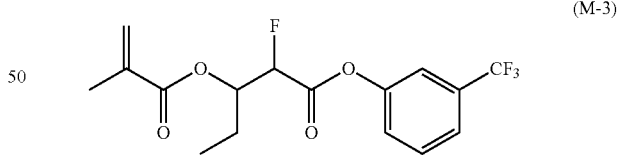

$^1$H-NMR (CDCl$_3$) δ: 1.20 (t, 3H; CH$_3$), 1.75-1.85 (m, 2H; CH$_2$—CH$_3$), 1.91 (s, 3H; CH$_3$), 4.86 (dd, 1H; CH—F), 5.45-5.65 (m, 1H; CH—CF$_2$), 5.68 (s, 1H; C=CH), 6.15 (s, 1H; C=CH$_2$), 7.30-7.70 (m, 4H; CH$_4$CF$_3$)

Example 4

Synthesis of 4-(trifluoromethyl)benzyl-2,2-difluoro-3-(methacryloyloxy)pentanoate (M-4)

After a reaction vessel which had been sufficiently dried inside by vacuum heating was replaced with dry nitrogen, 100 mL of a solution of 22.22 g (0.1 mol) of 2,2-difluoro-3-

(methacryloyloxy)pentanoic acid in dichloromethane was added into the reaction vessel, and the mixture was cooled to an ice temperature. Thereto was added 100 mL of a solution of 22.70 g (0.11 mol) of DCC in dichloromethane over 10 min, and 0.61 g (5 mmol) of DMAP and 18.49 g (0.105 mol) of 4-(trifluoromethyl)benzyl alcohol were further added. Thereafter, the temperature of the reaction vessel was elevated to the room temperature, followed by stirring the mixture for 2 hrs, and 300 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off with an evaporator, followed by purification by column chromatography to give 24.72 g of 4-(trifluoromethyl)benzyl-2,2-difluoro-3-(methacryloyloxy)pentanoate (M-4) (yield: 65%).

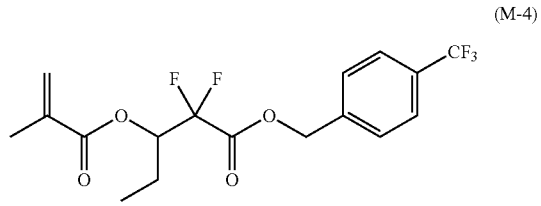 [SMILES: C=C(C)C(=O)OC(CC)C(F)(F)C(=O)OCc1ccc(C(F)(F)F)cc1]

(M-4)

$^1$H-NMR (CDCl$_3$) δ: 1.08 (t, 3H; CH$_3$), 1.75-1.85 (m, 2H; CH$_2$—CH$_3$), 1.97 (s, 3H, CH$_3$), 5.35 (s, 2H; Ar—CH$_2$), 5.45-5.65 (m, 1H; CH—CF$_2$), 5.65 (s, 1H; C=CH$_2$), 6.12 (s, 1H; C=CH$_2$), 7.16 (d, 2H; Ar), 7.55 (d, 2H; Ar)

Example 5

Synthesis of 2,2,2-trifluoroethyl-2,2-difluoro-3-(methacryloyloxy)pentanoate (M-5)

After a reaction vessel which had been sufficiently dried inside by vacuum heating was replaced with dry nitrogen, 100 mL of a solution of 22.22 g (0.1 mol) of 2,2-difluoro-3-(methacryloyloxy)pentanoic acid in dichloromethane was added into the reaction vessel, and the mixture was cooled to an ice temperature. Thereto was added 100 mL of a solution of 22.70 g (0.11 mol) of DCC in dichloromethane over 10 min, and 0.61 g (5 mmol) of DMAP and 10.40 g (0.105 mol) of 2,2,2-trifluoroethanol were further added. Thereafter, the temperature of the reaction vessel was elevated to the room temperature, followed by stirring the mixture for 2 hrs, and 300 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off with an evaporator, followed by purification by column chromatography to give 21.60 g of 2,2,2-trifluoroethyl-2,2-difluoro-3-(methacryloyloxy)pentanoate (M-5) (yield: 71%).

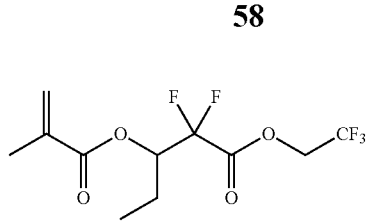

(M-5)

$^1$H-NMR (CDCl$_3$) δ: 0.98 (t, 3H; CH$_3$), 1.70-1.90 (m, 2H; CH$_2$—CH$_3$), 1.95 (s, 3H, CH$_3$), 4.62 (q, 2H; CH$_2$—CF$_3$), 5.35-5.45 (m, 1H; CH—CF$_2$), 5.67 (s, 1H; C=CH$_2$), 6.18 (s, 1H; C=CH$_2$)

Example 6

Synthesis of 1,1,1-trifluoro-3-oxo-3-(2,2,2-trifluoroethoxy)propan-2-yl methacrylate (M-6)

Under a nitrogen atmosphere, 50 mL of dehydrated THF, 5.56 g (55.0 mmol) of triethylamine and 305 mg (2.5 mmol) of dimethylaminopyridine were added to 7.20 g (50.0 mmol) of 3,3,3-trifluorolactic acid at a room temperature. Thereafter, 5.75 g (55.0 mmol) of methacrylic acid chloride was added dropwise over 10 min, and then the mixture was stirred for 2 hrs. After disappearance of the raw material was confirmed by TLC, an aqueous sodium bicarbonate solution was added to stop the reaction. Thereafter, ethyl acetate was added to the reaction liquid and extraction was carried out three times. The organic layer thus obtained was washed with water, saturated brine each once, and dried by adding anhydrous sodium sulfate. Thereafter, the solvent was distilled off under a reduced pressure, and the resulting product was purified by column chromatography to give 3.71 g of 3,3,3-trifluoro-2-(methacryloyloxy)propionic acid represented by the following formula in the form of pale yellow oil (yield: 35%).

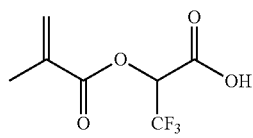

Under a nitrogen atmosphere, 3.18 g (15 mmol) of 3,3,3-trifluoro-2-(methacryloyloxy)propionic acid was added to 60 mL of a solution of 6.8 g (16.5 mmol) of DCC and 0.37 g (0.003 mol) of DMAP in dichloromethane, and 1.78 g (18 mmol) of 2,2,2-trifluoroethanol was added thereto at 0° C. The temperature of the mixture was equilibrated to the room temperature, and the mixture was stirred for 3 hrs. After disappearance of the raw material was confirmed by TLC, the reaction liquid was cooled to 0° C., and the reaction was stopped by adding 1 N hydrochloric acid. Thereafter, ethyl acetate was added to the reaction liquid and extraction was carried out three times, and the organic layer thus obtained was washed with water twice. Thereafter, purification by column chromatography gave 2.65 g of intended 1,1,1-trifluoro-3-oxo-3-(2,2,2-trifluoroethoxy)propan-2-yl methacrylate (M-6) (yield: 60%).

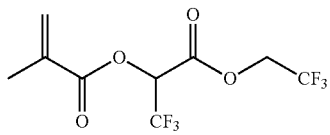
(M-6)

¹H-NMR (CDCl₃) δ: 1.87 (s, 3H, CH₃—C═), 4.60 (m, 2H; CH₂—CF₃), 5.50 (m, 1H, CH—CF₃), 5.55 (s, 1H, C═CH₂), 6.06 (s, 1H, C═CH₂)

Example 7

Synthesis of phenyl-2,2-difluoro-3-(methacryloyloxy)pentanoate (M-16)

After a reaction vessel which had been sufficiently dried inside by vacuum heating was replaced with dry nitrogen, 100 mL of a solution of 22.22 g (0.1 mol) of 2,2-difluoro-3-(methacryloyloxy)pentanoic acid on dichloromethane was added into the reaction vessel, and the mixture was cooled to an ice temperature. Thereto was added 100 mL of a solution of 22.70 g (0.11 mol) of dicyclohexylcarbodiimide (DCC) in dichloromethane over 10 min, and 0.61 g (5 mmol) of DMAP and 9.88 g (0.105 mol) of phenol were further added. Thereafter, the temperature of the reaction vessel was elevated to the room temperature, followed by stirring the mixture for 2 hrs, and 300 g of 1 N aqueous hydrochloric acid was added while intimately stirring. Subsequently, dichloromethane was separated by a separatory funnel, and the aqueous layer was extracted again with dichloromethane to obtain an extraction liquid. After the extraction liquid was combined with the dichloromethane layer and washed with 1 N aqueous hydrochloric acid, the solvent of the dichloromethane layer was distilled off with an evaporator, followed by purification by column chromatography to give 17.3 g of phenyl-2,2-difluoro-3-(methacryloyloxy)pentanoate (M-16) (yield: 58%).

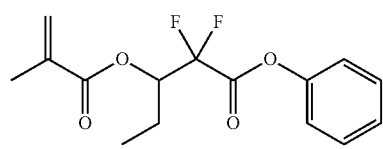
(M-16)

¹H-NMR (CDCl₃) δ: 1.00 (t, 3H; CH₃), 1.70-1.90 (m, 2H; CH₂—CH₃), 1.91 (s, 3H; CH₃), 5.45-5.65 (m, 1H; CH—CF₂), 5.68 (s, 1H; C═CH₂), 6.15 (s, 1H; C═CH₂), 6.80-7.15 (m, 5H; Ar)

Example 8

Synthesis of phenyl-3-oxo-3-(2,2,2-trifluoroethoxy) propan-2-yl methacrylate (M-17)

Under a nitrogen atmosphere, 3.18 g (15 mmol) of 3,3,3-trifluoro-2-(methacryloyloxy)propionic acid was added to 60 mL of a solution of 6.8 g (16.5 mmol) of DCC and 0.37 g (0.003 mol) of DMAP in dichloromethane, and 1.69 g (18 mmol) of phenol was added thereto at 0° C. The temperature of the mixture was equilibrated to the room temperature, and the mixture was stirred for 3 hrs. After disappearance of the raw material was confirmed by TLC, the reaction liquid was cooled to 0° C., and the reaction was stopped by adding 1 N hydrochloric acid. Thereafter, ethyl acetate was added to the reaction liquid and extraction was carried out three times, and the organic layer thus obtained was washed with water twice. Thereafter, purification by column chromatography gave 2.20 g of intended phenyl-3-oxo-3-(2,2,2-trifluoroethoxy) propan-2-yl methacrylate (M-17) (yield: 51%).

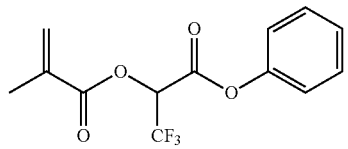
(M-17)

¹H-NMR (CDCl₃) δ: 1.90 (s, 3H, CH₃—C═), 5.55 (m, 1H, CH—CF₃), 5.60 (s, 1H, C═CH₂), 6.00 (s, 1H, C═CH₂), 7.00-7.60 (m, 5H, Ar)

<Synthesis of Polymer (A)>

Using the compounds represented by the above formulae (M-1) to (M-6), (M-16), (M-17) and the following formulae (M-7) to (M-12), respectively, (A-1) to (A-17) and (A'-1) were synthesized according to the following method.

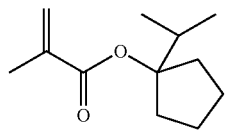
(M-7)

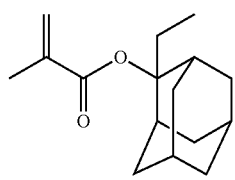
(M-8)

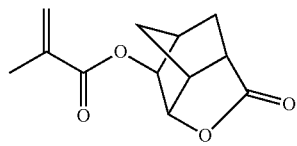
(M-9)

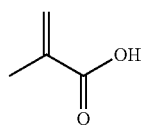
(M-10)

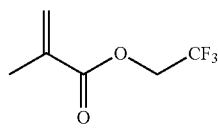
(M-11)

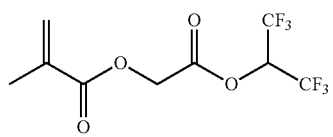
(M-12)

Example 9

The compound (M-7) in an amount of 1.23 g (6.24 mmol) and the compound (M-1) in an amount of 18.78 g (56.17 mmol) were dissolved in 40 g of 2-butanone, and therewith 0.51 g of dimethyl 2,2'-azobis(2-isobutyronitrile) was charged into a 200 mL three-neck flask. After the reactor vessel was purged with nitrogen for 30 min, it was heated to 80° C. while stirring the mixture. The time point at which the heating was started was defined as a polymerization starting time, and the polymerization reaction was performed for 5 hrs. After completing the polymerization, the polymerization solution was cooled to no higher than 30° C. by water cooling. The polymerization solution was concentrated in vacuo by an evaporator until the weight of the polymerization solution became 40 g. Thereafter, 40 g of methanol was charged, and the mixed Solution was transferred into a 500 mL separatory funnel which had been charged with 200 g of hexane. Liquid separating operation was carried out to recover the underlayer, and the solvent thereof was distilled off by an evaporator. The resulting solid was crushed to give a powder which was vacuum dried at 40° for 15 hrs. Thus, 12.0 g of a white powder (A-1) (yield: 60%) was obtained. The polymer had the Mw of 6,600, and the Mw/Mn of 1.45. As a result of a $^{13}$C-NMR analysis, the contents of the repeating unit derived from the compound (M-7) and the repeating unit derived from the compound (M-1) were 11.2 mol % and 88.8 mol %, respectively.

Examples 10 to 25 and Comparative Example 1

Using compounds shown in Table 1, (A-2) to (A-17) and (A'-1) were synthesized similarly to Example 9, and were defined as Examples 10 to 25 and Comparative Example 1, respectively. In addition, physical property values of each of them are also shown in Table 1.

TABLE 1

| | Polymer (A) | Compound blend amount type | Compound blend amount blend amount (mol %) | Content of structural unit in the polymer content (mol %) | Physical property value Mw | Physical property value Mw/Mn | content of fluorine atoms (% by mass) |
|---|---|---|---|---|---|---|---|
| Example 9 | (A-1) | (M-7) | 10 | 11.2 | 6,600 | 1.45 | 20.2 |
| | | (M-1) | 90 | 88.8 | | | |
| Example 10 | (A-2) | (M-2) | 100 | 100.0 | 4,900 | 1.4 | 25.9 |
| Example 11 | (A-3) | (M-7) | 10 | 11.0 | 7,000 | 1.58 | 23.1 |
| | | (M-2) | 90 | 89.0 | | | |
| Example 12 | (A-4) | (M-7) | 50 | 51.5 | 6,500 | 1.57 | 12.6 |
| | | (M-2) | 50 | 48.5 | | | |
| Example 13 | (A-5) | (M-7) | 10 | 10.2 | 7,000 | 1.5 | 20.4 |
| | | (M-9) | 10 | 11.0 | | | |
| | | (M-2) | 80 | 78.8 | | | |
| Example 14 | (A-6) | (M-8) | 20 | 21.1 | 7,100 | 1.55 | 20.5 |
| | | (M-2) | 80 | 78.9 | | | |
| Example 15 | (A-7) | (M-9) | 20 | 23.0 | 6,400 | 1.56 | 20.0 |
| | | (M-2) | 80 | 77.0 | | | |
| Example 16 | (A-8) | (M-11) | 30 | 28.9 | 6,800 | 1.6 | 28.2 |
| | | (M-2) | 70 | 71.1 | | | |
| Example 17 | (A-9) | (M-7) | 10 | 11.4 | 6,300 | 1.51 | 24.6 |
| | | (M-11) | 20 | 20.1 | | | |
| | | (M-2) | 70 | 68.5 | | | |
| Example 18 | (A-10) | (M-10) | 10 | 8.8 | 7,800 | 1.49 | 23.7 |
| | | (M-2) | 90 | 91.2 | | | |
| Example 19 | (A-11) | (M-7) | 20 | 21.0 | 7,000 | 1.48 | 18.3 |
| | | (M-10) | 10 | 8.3 | | | |
| | | (M-2) | 70 | 70.7 | | | |
| Example 20 | (A-12) | (M-7) | 10 | 11.0 | 9,000 | 1.55 | 19.4 |
| | | (M-3) | 90 | 89.0 | | | |
| Example 21 | (A-13) | (M-7) | 10 | 11.4 | 8,800 | 1.6 | 22.1 |
| | | (M-4) | 90 | 88.6 | | | |
| Example 22 | (A-14) | (M-7) | 10 | 11.4 | 8,900 | 1.42 | 27.7 |
| | | (M-5) | 90 | 88.6 | | | |
| Example 23 | (A-15) | (M-7) | 10 | 11.0 | 7,900 | 1.42 | 34.5 |
| | | (M-6) | 90 | 89.0 | | | |
| Example 24 | (A-16) | (M-7) | 10 | 11.5 | 8,400 | 1.51 | 11.3 |
| | | (M-16) | 90 | 88.5 | | | |
| Example 25 | (A-17) | (M-7) | 10 | 10.6 | 8,800 | 1.55 | 17.7 |
| | | (M-17) | 90 | 89.4 | | | |
| Comparative Example 1 | (A'-1) | (M-7) | 20 | 20.9 | 6,700 | 1.5 | 30.7 |
| | | (M-12) | 80 | 79.1 | | | |

<Synthesis of Polymer (C)>

Using compounds represented by the following formulae (M-13) to (M-15), and the compounds selected from the above (M-8) and (M-9), (C-1) and (C-2) were synthesized according to the following method.

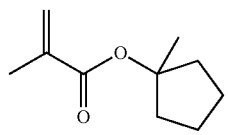

(M-13)

-continued

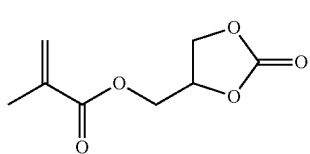
(M-14)

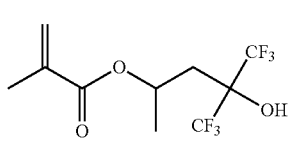
(M-15)

Synthesis Example 1

A monomer solution was prepared by dissolving 86.61 g (0.515 mol) of the compound (M-13), 68.65 g (0.309 mol) of the compound (M-9) and 19.17 g (0.103 mol) of the compound (M-14) in 400 g of 2-butanone, and further adding 8.45 g of dimethyl 2,2'-azobis(2-isobutyronitrile). The compound (M-8) in an amount of 25.57 g (0.103 mol) was charged into a 2,000 mL three-neck flask, and 200 g of 2-butanone was further charged to permit dissolution. After the reactor vessel was purged with nitrogen for 30 min, it was heated to 80° C. while stirring the mixture, and thereto was added dropwise the monomer solution prepared beforehand using a dripping funnel over 3 hrs. The time point at which the dropwise addition was started was defined as a polymerization starting time, and the polymerization reaction was performed for 6 hrs. After completing the polymerization, the polymerization solution was cooled to no higher than 30° C. by water cooling. A white powder precipitated by charging the solution into 4,000 g of methanol was filtered off. The white powder obtained by filtration was dispersed methanol to give a slurry state, followed by washing and filtration. Such an operation was repeated twice, followed by drying at 60° C. for 15 hrs to obtain a copolymer (C-1) as a white powder (150.6 g, yield: 75.3%). This copolymer had an Mw of 6,700 and Mw/Mn of 1.40, and as a result of a $^{13}$C-NMR analysis, had the content (mol %) of each of the repeating units derived from the compound (M-13), the compound (M-8), the compound (M-9) and the compound (M-14) of 49.0:9.2:31.6:10.1.

Synthesis Example 2

A monomer solution was prepared by dissolving 86.61 g (0.515 mol) of the compound (M-13), 68.65 g (0.309 mol) of the compound (M-9) and 30.39 g (0.103 mol) of the compound (M-15) in 400 g of 2-butanone, and further adding 8.45 g of dimethyl 2,2'-azobis(2-isobutyronitrile). The compound (M-8) in an amount of 25.57 g (0.103 mol) was charged into a 2,000 mL three-neck flask, and 200 g of 2-butanone was further charged to permit dissolution. After the reactor vessel was purged with nitrogen for 30 min, it was heated to 80° C. while stirring the mixture, and thereto was added dropwise the monomer solution prepared beforehand using a dripping funnel over 3 hrs. The time point at which the dropwise addition was started was defined as a polymerization starting time, and the polymerization reaction was performed for 6 hrs. After completing the polymerization, the polymerization solution was cooled to no higher than 30° C. by water cooling. A white powder precipitated by charging the solution into 4,000 g of methanol was filtered off. The white powder obtained by filtration was dispersed methanol to give a slurry state, followed by washing and filtration. Such an operation was repeated twice, followed by drying at 60° C. for 15 hrs to obtain a copolymer (C-2) as a white powder (131 g, yield: 65.5%). This copolymer had an Mw of 5,500 and Mw/Mn of 1.401, and as a result of a $^{13}$C-NMR analysis, had the content (mol %) of each of the repeating units derived from the compound (M-13), the compound (M-8), the compound (M-9) and the compound (M-15) of 51.7:8.3:30.8:9.2. The content of fluorine was 3.56% by mass.

<Preparation of Radiation-Sensitive Resin Composition>

The acid generator (B), the acid diffusion control agent and the solvent for constituting the radiation-sensitive resin composition are shown below.

(B-1) to (B-4) used as the acid generator (B) are represented by the following formulae.

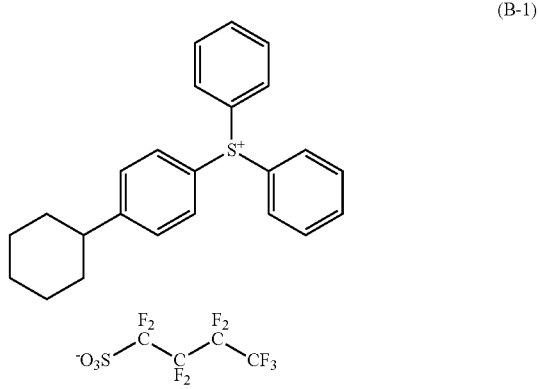
(B-1)

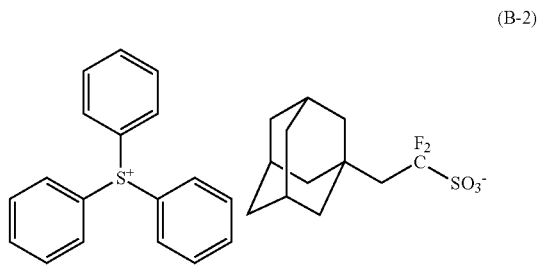
(B-2)

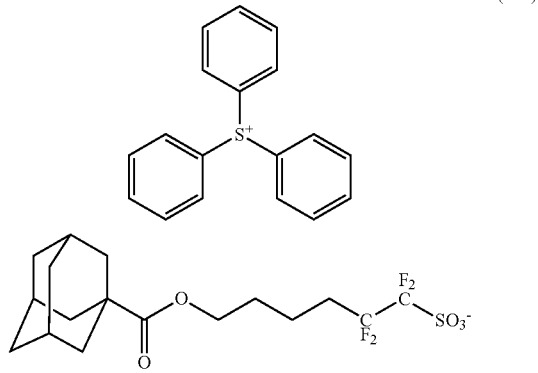
(B-3)

-continued

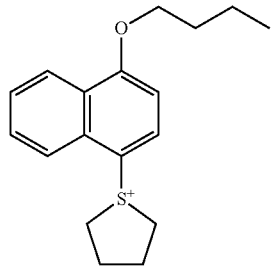
(B-4)

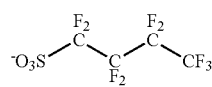

(D-1) to (D-3) used as the acid diffusion control agent are represented by the following formulae.

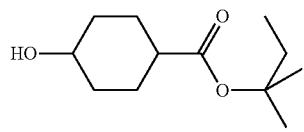
(D-1)

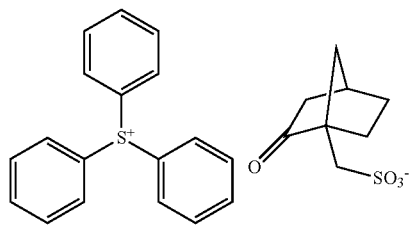
(D-2)

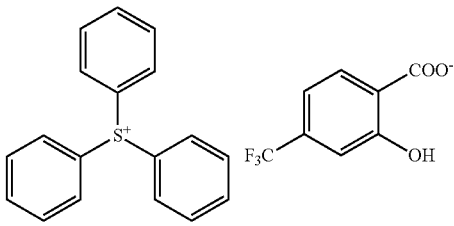
(D-3)

Example 26

A composition solution of a radiation-sensitive resin composition was prepared by mixing 5.0 parts by mass of the polymer (A-1), 9.0 parts by mass of the acid generating agent (B-1), 100 parts by mass of the polymer (C-1), 5.6 parts by mass of the acid diffusion control agent (D-2), 100 parts by mass of γ-butyrolactone as an additive, and 1,500 parts by mass of propylene glycol monomethyl ether acetate and 650 parts by mass of cyclohexanone as a solvent.

Examples 27 to 47, and Comparative Example 2

A composition solution of each radiation-sensitive resin composition was prepared in a similar manner to Example 26 except that each component was blended as shown in Table 2, and was each defined as Examples 27 to 47 and Comparative Example 2.

TABLE 2

| Radiation-sensitive resin composition | Polymer (A) type | Polymer (A) blend amount (parts by mass) | Acid generator (B) type | Acid generator (B) blend amount (parts by mass) | Polymer (C) type | Polymer (C) blend amount (parts by mass) | Acid diffusion control agent type | Acid diffusion control agent blend amount (parts by mass) |
|---|---|---|---|---|---|---|---|---|
| Example 26 | (A-1) | 5.0 | (B-1) | 9.0 | (C-1) | 100.0 | (D-2) | 5.6 |
| Example 27 | (A-2) | 5.0 | (B-1) | 9.0 | (C-1) | 100.0 | (D-2) | 5.6 |
| Example 28 | (A-3) | 5.0 | (B-1) | 9.0 | (C-1) | 100.0 | (D-2) | 5.6 |
| Example 29 | (A-4) | 5.0 | (B-1) | 9.0 | (C-1) | 100.0 | (D-2) | 5.6 |
| Example 30 | (A-5) | 5.0 | (B-1) | 9.0 | (C-1) | 100.0 | (D-2) | 5.6 |
| Example 31 | (A-6) | 5.0 | (B-1) | 9.0 | (C-1) | 100.0 | (D-2) | 5.6 |
| Example 32 | (A-7) | 5.0 | (B-1) | 9.0 | (C-1) | 100.0 | (D-2) | 5.6 |
| Example 33 | (A-8) | 5.0 | (B-1) | 9.0 | (C-1) | 100.0 | (D-2) | 5.6 |
| Example 34 | (A-9) | 5.0 | (B-1) | 9.0 | (C-1) | 100.0 | (D-2) | 5.6 |
| Example 35 | (A-10) | 5.0 | (B-1) | 9.0 | (C-1) | 100.0 | (D-2) | 5.6 |
| Example 36 | (A-11) | 5.0 | (B-1) | 9.0 | (C-1) | 100.0 | (D-2) | 5.6 |
| Example 37 | (A-12) | 5.0 | (B-1) | 9.0 | (C-1) | 100.0 | (D-2) | 5.6 |
| Example 38 | (A-13) | 5.0 | (B-1) | 9.0 | (C-1) | 100.0 | (D-2) | 5.6 |
| Example 39 | (A-14) | 5.0 | (B-1) | 9.0 | (C-1) | 100.0 | (D-2) | 5.6 |
| Example 40 | (A-15) | 5.0 | (B-1) | 9.0 | (C-1) | 100.0 | (D-2) | 5.6 |
| Example 41 | (A-16) | 5.0 | (B-1) | 9.0 | (C-1) | 100.0 | (D-2) | 5.6 |
| Example 42 | (A-17) | 5.0 | (B-1) | 9.0 | (C-1) | 100.0 | (D-2) | 5.6 |
| Example 43 | (A-3) | 5.0 | (B-3) (B-4) | 5.0 4.0 | (C-1) | 100.0 | (D-2) | 5.6 |
| Example 44 | (A-14) | 5.0 | (B-2) (B-3) | 5.0 4.0 | (C-1) | 100.0 | (D-2) | 5.6 |
| Example 45 | (A-14) | 5.0 | (B-2) (B-3) | 3.0 11.0 | (C-1) | 100.0 | (D-3) | 6.1 |
| Example 46 | (A-14) | 5.0 | (B-2) (B-3) | 3.0 11.0 | (C-1) | 100.0 | (D-1) | 1.7 |
| Example 47 | (A-2) | 5.0 | (B-2) (B-3) | 3.0 11.0 | (C-2) | 100.0 | (D-1) | 1.7 |
| Comparative Example 2 | (A'-1) | 5.0 | (B-2) (B-3) | 3.0 11.0 | (C-1) | 100.0 | (D-2) | 5.6 |

<Evaluation>

Resist coating films were formed with the radiation-sensitive resin compositions of Examples 26 to 47 and Comparative Example 2, and evaluations were made on the dynamic contact angle and development defects, according to each method described below. The results of the evaluations are shown in Table 3.

[Measurement of Receding Contact Angle]

A coating film was formed on a substrate using the radiation-sensitive resin composition. Thereafter, a receding contact angle of the coating film thus formed were measured under a condition involving a room temperature of 23° C., a humidity of 45% and an ordinary pressure, using "DSA-10" of KRUS Electronics Ltd., according to the following procedure.

The needle of DSA-10 was washed with acetone and isopropyl alcohol prior to the measurement, and water was introduced into the needle. The wafer was placed on the wafer stage, and the height of the stage was adjusted such that the distance between the surface of wafer ant the needle tip of no greater than 1 mm was provided. Next, after water was discharged from the needle to form a water droplet of 25 μL on the wafer, the water droplet was aspirated by the needle at a rate of 10 μL/min for 180 sec, and the contact angle was concomitantly measured every second. A mean value of the contact angles at 20 points was calculated after a contact angle was stably measured to determine the receding contact angle)(°).

On an 8 inch silicon wafer was formed a coating film having a film thickness of 110 nm with the radiation-sensitive resin composition, and soft baking (SB) was carried out at 120° C. for 50 sec. The receding contact angle of the substrate was defined as "post SB receding contact angle".

On an 8 inch silicon wafer was formed a coating film having a film thickness of 110 nm with the radiation-sensitive resin composition, and SB was carried out at 120° C. for 50 sec. Thereafter, the film was developed with a 2.38% by mass aqueous tetramethylammoniumhydroxide solution for 10 sec using a GP nozzle attached to a development apparatus of CLEAN TRACK "ACT8" manufactured by Tokyo Electron Limited, followed by rinsing with pure water for 15 sec and spin drying at 2,000 rpm. The receding contact angle of the resulting substrate was defined as "after development for 10 sec".

On an 8 inch silicon wafer was formed a coating film having a film thickness of 110 nm with the radiation-sensitive resin composition, and SB was carried out at 120° C. for 50 sec. Thereafter, the film was developed with a 2.38% by mass aqueous tetramethylammoniumhydroxide solution using a GP nozzle of a development system CLEAN TRACK "ACT8" manufactured by Tokyo Electron Limited for 30 sec, and rinsed with pure water for 30 sec, followed by spin drying at 2,000 rpm. The receding contact angle of the resulting substrate was defined as "after development for 30 sec".

[Measurement of Contact Angle After Storage for Three Months]

The prepared resist was stored at 23° C. for three months, and the receding contact angle was measured according to the identical method to that of the "post SB receding contact angle" described above, and the value was defined as "contact angle after storage for three months".

[Development Characteristic]

A coating film having a film thickness of 110 nm was formed with the radiation-sensitive resin composition on a silicon wafer having a diameter of 12 inches on which an underlayer antireflective film (Nissan Chemical Industries, Ltd., ARC66) had been formed, and soft-baking (SB) was carried out at 120° C. for 50 sec. Next, this coating film was exposed through a line-and-space mask pattern (1L/1S) with a target size of a width of 45 nm using an ArF excimer laser Immersion Scanner (NIKON Corporation, NSR S610C) under a condition including NA of 1.3, ratio of 0.800, and Dipole. After the exposure, post-exposure baking (PEB) was carried out at 95° C. for 50 sec. Thereafter, the coating film was developed with a 2.38% by mass aqueous tetramethylammoniumhydroxide solution for 10 sec using a GP nozzle attached to a development apparatus CLEAN TRACK "ACT8" manufactured by Tokyo Electron Limited, followed by rinsing with pure water for 15 sec and spin drying at 2,000 rpm to form a positive type resist pattern. According to this procedure, an exposure dose at which a 1L/1S pattern having a line width of 45 nm was formed was determined to be an optimum exposure dose. A 1L/1S pattern having a line width of 45 nm was formed on the entire surface of the wafer with the optimal exposure dose, and the wafer was employed as a wafer for inspection of defects. It is to be noted that a scanning electron microscope (Hitachi High-Technologies Corporation, CC-4000) was used for the measurement of line-width. Thereafter, the number of defects on the wafer for inspection of defects was counted using KLA2810 of KLA-Tencor Corporation. Furthermore, the defects counted using KLA2810 of KLA-Tencor Corporation were classified into the defects judged to be derived from the resist, and those resulting from foreign substances derived from the outside. After the classification, with respect to a total number of defects judged to be derived from the resist coating film, the evaluation was made as: "A (favorable)" when the total number was less than 100/wafer; "B (somewhat favorable)" when the total number was from 100 to 500/wafer, and "C (unfavorable)" when the total number was greater than 500/wafer.

TABLE 3

| Radiation-sensitive resin composition | Receding contact angle (°) | | | Development defect | Receding contact angle after storage for three months (°) |
| --- | --- | --- | --- | --- | --- |
| | post SB | after development for 10 sec | after development for 30 sec | | |
| Example 26 | 80 | <15 | <15 | A | alteration not found |
| Example 27 | 82 | <15 | <15 | A | alteration not found |
| Example 28 | 81 | <15 | <15 | A | alteration not found |
| Example 29 | 80 | <15 | <15 | A | alteration not found |
| Example 30 | 74 | <15 | <15 | A | alteration not found |
| Example 31 | 82 | <15 | <15 | A | alteration not found |
| Example 32 | 78 | <15 | <15 | A | alteration not found |
| Example 33 | 84 | <15 | <15 | A | alteration not found |
| Example 34 | 84 | <15 | <15 | A | alteration not found |
| Example 35 | 72 | <15 | <15 | A | alteration not found |
| Example 36 | 72 | <15 | <15 | A | alteration not found |
| Example 37 | 81 | <15 | <15 | A | alteration not found |
| Example 38 | 80 | <15 | <15 | A | alteration not found |
| Example 39 | 84 | <15 | <15 | A | alteration not found |
| Example 40 | 81 | <15 | <15 | A | alteration not found |
| Example 41 | 75 | <15 | <15 | A | alteration not found |
| Example 42 | 80 | <15 | <15 | A | alteration not found |
| Example 43 | 81 | <15 | <15 | A | alteration not found |
| Example 44 | 85 | <15 | <15 | A | alteration not found |
| Example 45 | 84 | <15 | <15 | A | alteration not found |
| Example 46 | 84 | <15 | <15 | A | alteration not found |
| Example 47 | 83 | <15 | <15 | A | alteration not found |
| Comparative Example 2 | 81 | 40 | 25 | C | alteration not found |

From the results shown in Table 3, it was ascertained that Examples 26 to 47 exhibited the post SB receding contact angle significantly decreased after development for 10 sec and after development for 30 sec, as compared with Comparative Example 2. In addition, inhibition of generation of development defects was also ascertained. Furthermore, in the case of the compositions of Examples 26 to 47, the difference between "post SB contact angle" and "contact angle after storage for three months" was scarcely found, indicating high storage stability.

INDUSTRIAL APPLICABILITY

Since the radiation-sensitive resin composition of the present invention contains a polymer having a specific structural unit and a radiation-sensitive acid generator, the resist coating film formed in a liquid immersion lithography process exerts a characteristic feature of having an adequately great dynamic contact angle in exposure and a significantly decreased dynamic contact angle after the development with an alkali, and shortening of the time period required for change in a dynamic contact angle is also enabled. As a result, in addition to suppression of elution of an acid generating agent and the like from the resist coating film, due to the surface of the coating film having a superior water breaking property, high speed scanning exposure is enabled, and occurrence of development defects is inhibited since an affinity to a developer is increased in development. Accordingly, a favorable resist pattern can be formed. Therefore, the radiation-sensitive resin composition can be suitably used as a chemically amplified resist for use in manufacture of semiconductor devices, particularly a resist for liquid immersion lithography.

The invention claimed is:

1. A radiation-sensitive resin composition comprising:

(A) a polymer comprising:

a structural unit (I) represented by formula (1); and at least one structural unit selected from the group consisting of a structural unit (II) represented by formula (2) and a structural unit (III) represented by formula (3); and (B) a radiation-sensitive acid generator:

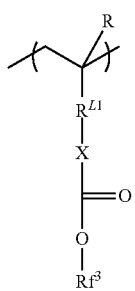

wherein, in the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a bivalent hydrocarbon group having 1 to 20 carbon atoms and having at least one fluorine atom,

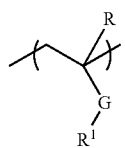

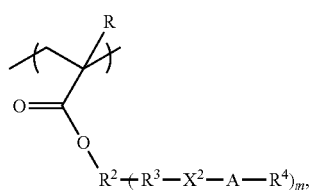

wherein:
in the formulae (2) and (3), R represents a hydrogen atom, a methyl group or a trifluoromethyl group;
in the formula (2), G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom; and
in the formula (3), $R^2$ represents a hydrocarbon group having a valency of (m+1) and having 1 to 20 carbon atoms, or a group in which an oxygen atom, a sulfur atom, —NR'—, a carbonyl group, —CO—O— or —CO—NH— is bound to a hydrocarbon group having a valency of (m+1) and having 1 to 20 carbon atoms at an end of $R^3$ side, wherein R' represents a hydrogen atom or a monovalent organic group; $R^3$ represents a single bond, a bivalent chain hydrocarbon group having 1 to 10 carbon atoms or a bivalent alicyclic hydrocarbon group having 4 to 20 carbon atoms; $X^2$ represents a bivalent chain hydrocarbon group having 1 to 20 carbon atoms and having at least one fluorine atom; A represents an oxygen atom, —NR"—, —CO—O—* or —SO$_2$—O—*, wherein R" represents a hydrogen atom or a monovalent organic group and * denotes a site bound to $R^4$; $R^4$ represents an acid-dissociable group or an alkali-dissociable group; and m is an integer of 1 to 3, wherein in a case where m is 2 or 3, a plurality of $R^3$s, $X^2$s, As and $R^4$s are each independent.

2. The radiation-sensitive resin composition according to claim 1, wherein the structural unit (I) is a structural unit (I-1) represented by formula (1-1):

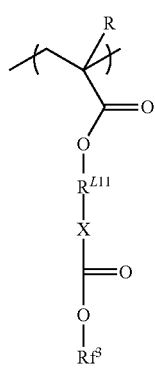

wherein, in the formula (1-1), $R^{L11}$ represents a single bond or a bivalent linking group; and R, $Rf^3$ and X are as defined in the formula (1).

3. The radiation-sensitive resin composition according to claim 2, wherein the structural unit (I-1) is at least one selected from the group consisting of structural units each represented by formulae (1-1a) to (1-1e):

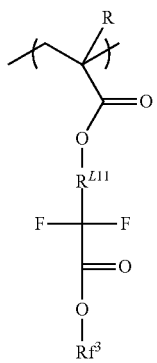
(1-1a)

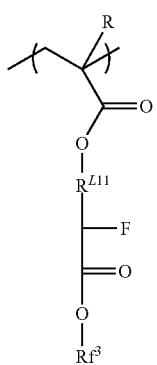
(1-1b)

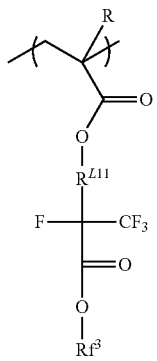
(1-1c)

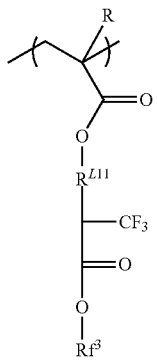
(1-1d)

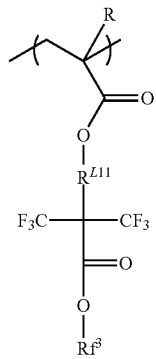
(1-1e)

wherein, in the formulae (1-1a) to (1-1e), R, $R^{L11}$ and $Rf^3$ are as defined in the formula (1-1).

4. The radiation-sensitive resin composition according to claim 1, wherein the $Rf^3$ is at least one selected from the set consisting of groups each represented by formulae ($Rf^3$-a) to ($Rf^3$-d):

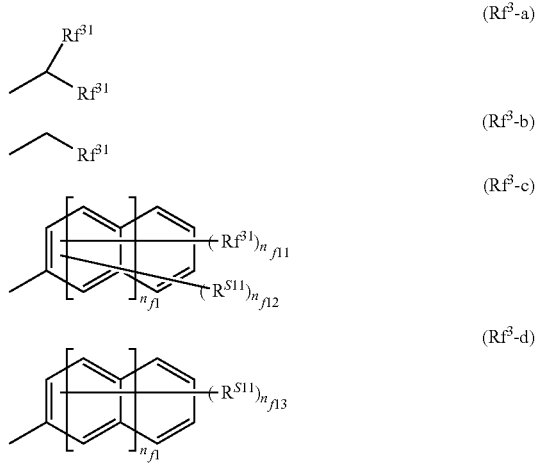

wherein, in the formulae ($Rf^3$-a) to ($Rf^3$-d), $Rf^{31}$ each independently represents a monovalent organic group having a fluorine atom; $R^{s11}$ each independently represents a substituent; $n_{f1}$ is each independently 0 or 1; $n_{f11}$ is an integer of 1 to $(5+2n_{f1})$; $n_{f12}$ is an integer of 0 to $(5+2n_{f1})$, wherein an inequality of: $(n_{f11}+n_{f12}) \leq (5+2n_{f1})$ is satisfied; and $n_{f13}$ is an integer of 0 to $(5+2n_{f1})$.

5. The radiation-sensitive resin composition according to claim 1, wherein the content of the structural unit (I) in the polymer (A) is no less than 30 mol % and no greater than 100 mol %.

6. The radiation-sensitive resin composition according to claim 1 further comprising (C) a polymer having a content of fluorine atoms less than a content of fluorine atoms of the polymer (A), the polymer (C) comprising an acid-dissociable group.

7. The radiation-sensitive resin composition according to claim 6, wherein the content of the polymer (A) is no less than 0.1 parts by mass and no greater than 10 parts by mass with respect to 100 parts by mass of the polymer (C).

8. A method for forming a resist pattern comprising:
forming a photoresist film on a substrate using the radiation-sensitive resin composition according to claim 1;

subjecting the photoresist film to liquid immersion lithography; and forming a resist pattern by developing the photoresist film subjected to the liquid immersion lithography.

9. The radiation-sensitive resin composition according to claim 1, wherein the content of the structural unit (II) in the polymer (A) is from 5 mol % to 30 mol %.

10. The radiation-sensitive resin composition according to claim 1, wherein the polymer (A) comprises the structural unit (III) represented by the formula (3), and at least one $R^4$ represents an acid-dissociable group.

11. The radiation-sensitive resin composition according to claim 1, wherein the polymer (A) comprises the structural unit (III) represented by the formula (3), and at least one $R^4$ represents an alkali-dissociable group.

12. The radiation-sensitive resin composition according to claim 1, wherein in the formula (3), m is 2 or 3.

13. A polymer comprising:
a structural unit (I) represented by formula (1); and
at least one structural unit selected from the group consisting of a structural unit (II) represented by formula (2) and a structural unit (III) represented by formula (3):

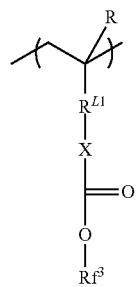

(1)

wherein, in the formula (1), R represents a hydrogen atom, a methyl group or a trifluoromethyl group; $R^{L1}$ represents a bivalent linking group; $Rf^3$ represents a monovalent aromatic hydrocarbon group which does not have or optionally has a substituent, a monovalent chain hydrocarbon group having a fluorine atom, or a monovalent alicyclic hydrocarbon group having a fluorine atom; and X represents a bivalent hydrocarbon group having 1 to 20 carbon atoms and having at least one fluorine atom,

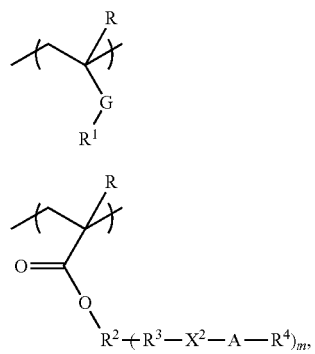

(2)

(3)

wherein:
in the formulae (2) and (3), R represents a hydrogen atom, a methyl group or a trifluoromethyl group;

in the formula (2), G represents a single bond, an oxygen atom, a sulfur atom, —CO—O—, —SO$_2$—O—NH—, —CO—NH—, or —O—CO—NH—; and $R^1$ represents a monovalent chain hydrocarbon group having 1 to 6 carbon atoms and having at least one fluorine atom, or a monovalent alicyclic hydrocarbon group having 4 to 20 carbon atoms and having at least one fluorine atom; and in the formula (3), $R^2$ represents a hydrocarbon group having a valency of (m+1) and having 1 to 20 carbon atoms, or a group in which an oxygen atom, a sulfur atom, —NR'—, a carbonyl group, —CO—O— or —CO—NH— is bound to a hydrocarbon group having a valency of (m+1) and having 1 to 20 carbon atoms at an end of $R^3$ side, wherein R' represents a hydrogen atom or a monovalent organic group; $R^3$ represents a single bond, a bivalent chain hydrocarbon group having 1 to 10 carbon atoms or a bivalent alicyclic hydrocarbon group having 4 to 20 carbon atoms; $X^2$ represents a bivalent chain hydrocarbon group having 1 to 20 carbon atoms and having at least one fluorine atom; A represents an oxygen atom, —NR"—, —CO—O—*  or —SO$_2$—O—*, wherein R" represents a hydrogen atom or a monovalent organic group and * denotes a site bound to $R^4$; $R^4$ represents an acid-dissociable group or an alkali-dissociable group; and m is an integer of 1 to 3, wherein in a case where m is 2 or 3, a plurality of $R^a$s, $X^2$s, As and $R^4$s are each independent.

14. The polymer according to claim 13, wherein the structural unit (I) is a structural unit (I-1) represented by formula (1-1):

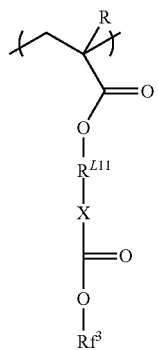

(1-1)

wherein, in the formula (1-1), $R^{L11}$ represents a single bond or a bivalent linking group; and R, $Rf^3$ and X are as defined in the formula (1).

15. The polymer to claim 14, wherein the structural unit (I-1) is at least one selected from the group consisting of structural units each represented by formulae (1-1a) to (1-1e):

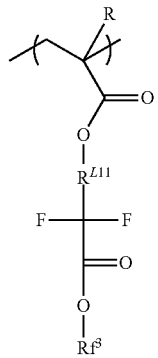

(1-1a)

-continued (1-1b)
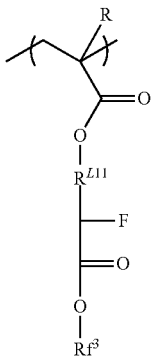

(1-1c)
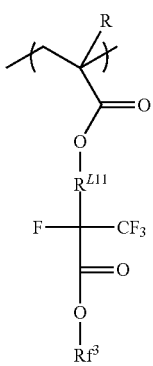

(1-1d)
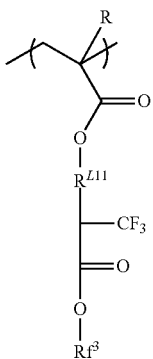

(1-1e)
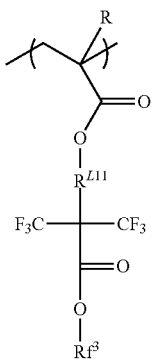

wherein, in the formulae (1-1a) to (1-1e), R, $R^{L11}$ and $Rf^3$ are as defined in the formula (1-1).

16. The polymer according to claim 13, wherein the $Rf^3$ is at least one selected from the set consisting of groups each represented by formulae ($Rf^3$-a) to ($Rf^3$-d):

($Rf^3$-a)

($Rf^3$-b)

($Rf^3$-c)
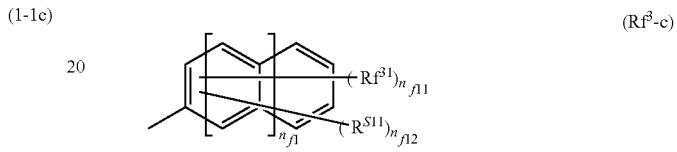

($Rf^3$-d)
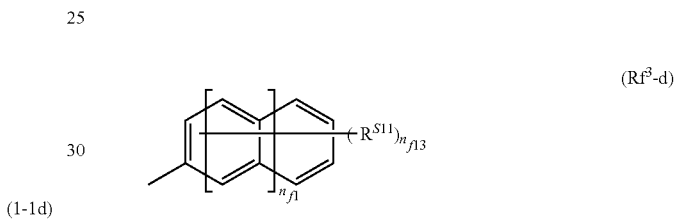

wherein, in the formulae ($Rf^3$-a) to ($Rf^3$-d), $Rf^{31}$ each independently represents a monovalent organic group having a fluorine atom; $R^{S11}$ each independently represents a substituent; $n_{f1}$ is each independently 0 or 1; $n_{f11}$ is an integer of 1 to $(5+2n_{f1})$; $n_{f12}$ is an integer of 0 to $(5+2n_{f1})$, wherein an inequality of: $(n_{f11}+n_{f12})<(5+2n_{f1})$ is satisfied; and $n_{f13}$ is an integer of 0 to $(5+2n_{f1})$.

17. The polymer according to claim 13, wherein the content of the structural unit (I) in the polymer is no less than 30 mol % and no greater than 100 mol %.

18. The polymer according to claim 13, wherein the content of the structural unit (II) in the polymer is from 5 mol % to 30 mol %.

19. The polymer according to claim 13, wherein the polymer comprises the structural unit (III) represented by the formula (3), and at least one $R^4$ represents an acid-dissociable group.

20. The polymer according to claim 13, wherein the polymer comprises the structural unit (III) represented by the formula (3), and at least one $R^4$ represents an alkali-dissociable group.

21. The polymer according to claim 13, wherein in the formula (3), m is 2 or 3.

* * * * *